(12) United States Patent
Cotten et al.

(10) Patent No.: US 6,797,506 B1
(45) Date of Patent: Sep. 28, 2004

(54) RECOMBINANT, REPLICATION DEFECTIVE CELO VIRUS AND CELO VIRUS DNA

(75) Inventors: Matthew Cotten, Vienna (AT); Jolanta Glotzer, Vienna (AT); Anne-Isabelle Michou, Strasbourg (FR)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 244 days.

(21) Appl. No.: 09/688,371

(22) Filed: Oct. 12, 2000

Related U.S. Application Data

(60) Provisional application No. 60/167,770, filed on Nov. 29, 1999.

(30) Foreign Application Priority Data

Oct. 13, 1999 (EP) .............................................. 99120358

(51) Int. Cl.[7] .............................. C12N 7/01; C12N 7/04; C12N 15/00; C12N 15/09; C12N 15/86; C12N 15/861; C07H 21/04

(52) U.S. Cl. ................. 435/235.1; 435/236; 435/320.1; 536/23.72

(58) Field of Search .............................. 435/235.1, 236, 435/320.1, 91.41, 91.42; 536/23.72, 23.1; 424/199.1, 205.1, 233.1

(56) References Cited

U.S. PATENT DOCUMENTS 6,335,016 B1 * 1/2002 Baker et al. ............. 424/199.1

FOREIGN PATENT DOCUMENTS

WO    WO 97/40180    * 10/1997

OTHER PUBLICATIONS

Michou et al. Journal of Virology. 1999; 73 (2): 1399–1410.*

Baker, A., et al., "Polyethylenimine (PEI) is a simple, inexpensive and effective reagent for condensing and linking plasmid DNA to adneovirus for gene delivery," *Gene Ther. 4*:773–782, Stockton Press (1997).

Bett, A.J., et al., "An efficient and flexible system for construction of adenovirus vectors with insertions or deletions in early regions 1 and 3," *Proc. Natl. Acad. Sci. USA 91*:8802–8806, The National Academy of Sciences of the USA (1994).

Boussif, O., et al., "A versatile vector for gene and oligonucleotide transfer into cells in culture and in vivo: Polyethylenimine," *Proc. Natl. Acad. Sci. USA 92*:7297–7301, The National Academy of Sciences of the USA (1995).

Buge, S.L., et al., "An Adenovirus–Simian Immunodeficiency Virus env Vaccine Elicits Humoral, Cellular, and Mucosal Immune Responses in Rhesus Macaques and Decreases Viral Burden following Vaginal Challenge," *J. Virol. 71*:8531–8541, American Society for Microbiology (1997).

Caravokyri, C., and K.N. Leppard, "Constitutive Episomal Expression of Polypeptide IX (pIX) in a 293–Based Cell Line Complements the Deficiency of pIX Mutant Adenovirus Type 5," *J. Virol. 69*:6627–6633, American Society for Microbiology (1995).

Celli, G., et al., "Soluble dominant–negative receptor uncovers essential roles for fibroblast growth factors in multi–organ induction and patterning," *EMBO J. 17*:1642–1655, Oxford University Press (Mar., 1998).

Chartier, C., et al., "Efficient Generation of Recombinant Adenovirus Vectors by Homologous Recombination in *Escherichia coli,*" *J. Virol. 70*:4805–4810, American Society for Microbiology (1996).

Chiocca, S., et al., "The Complete DNA Sequence and Genomic Organization of the Avian Adenovirus CELO," *J. Virol. 70*:2939–2949, American Society for Microbiology (1996).

Chiocca, S., et al., "Identification of a Novel Antiapoptotic Protein, GAM–1, Encoded by the CELO Adenovirus," *J. Virol. 71*:3168–3177, American Society for Microbiology (1997).

Colby, W.W., and Shenk, T., "Adenovirus Type 5 Virions Can Be Assembled In Vivo in the Absence of Detectable Polypeptide IX," *J. Virol. 39*:977–980, American Society for Microbiology (1981).

Cotten, M., et al., "Chicken Adenovirus (CELO Virus) Particles Augment Receptor–Mediated DNA Delivery to Mammalian Cells and Yield Exceptional Levels of Stable Transformants," *J. Virol. 67*:3777–3785, American Society for Microbiology (1993).

Cowen, B., et al., "Avian Adenoviruses: Effect on Egg Production, Shell Quality, and Feed Consumption," *Avian Diseases 22*:459–470, The American Association of Avian Pathologists (1978).

Crouzet, J., et al., "Recombinational construction in *Escherichia coli* of infectious adenoviral genomes," *Proc. Natl. Acad. Sci. USA 94*:1414–1419, The National Academy of Sciences of the USA (1997).

(List continued on next page.)

*Primary Examiner*—Shanon Foley
(74) *Attorney, Agent, or Firm*—Sterne, Kessler, Goldstein & Fox PLLC

(57) ABSTRACT

Recombinant CELO virus or CELO virus DNA with a deletion or disruption of the Gam1 gene, optionally combined with deletions at the right or left end of the viral genome that allow insertion of large pieces of foreign DNA. The virus is useful as a vaccine for animals, in particular birds, and for gene therapy and vaccine applications in humans. The virus can also be used for recombinant protein production.

30 Claims, 11 Drawing Sheets

OTHER PUBLICATIONS

DeGregori, J., et al., "Distinct roles for E2F proteins in cell growth control and apoptosis," *Proc. Natl. Acad. Sci. USA 94:*7245–7250, The National Academy of Sciences of the USA (1997).

Degryse, E., "In vivo intermolecular recombination in *Escherichia coli:* application to plasmid constructions," *Gene 170:*45–50, Elsevier Science B.V. (1996).

de Quinto, S. L. and Martinez–Salas, E., "Parameters influencing translational efficiency in aphthovirus IRES–based bicistronic expression vectors," *Gene 217:*51–56, Elsevier Science B.V. (Sep., 1998).

de Wet, J.R., et al., "Firefly Luciferase Gene: Structure and Expression in Mammalian Cells," *Mol. Cell. Biol. 7:*725–737, American Society for Microbiology (1987).

Evan, G.I. et al., "Isolation of Monoclonal Antibodies Specific for Human c–myc Proto–Oncogene Product," *Mol. Cell. Biol. 5:*3610–3616, American Society for Microbiology (1985).

Fisher, K. J., et al., "Recombinant Adenovirus Deleted of All Viral Genes for Gene Therapy of Cystic Fibrosis," *Virol. 217:*11–22, Academic Press (1996).

Gerber, H.–P., et al., "VEGF is required for growth and survival in neonatal mice," *Develop. 126:*1149–1159, The Company of Biologists Limited (Mar., 1999).

Gerdts, V., et al., "Protection of pigs against Aujeszky's disease by DNA vaccination," *J. Gen. Virol. 78:*2139–2146, Society for General Microbiology (1997).

Ghosh–Choudhury, G., et al., "Protein IX, a minor component of the human adenovirus capsid, is essential for the packaging of full length genomes," *EMBO J. 6:*1733–1739, IRL Press (1987).

Gluzman, Y., et al., "Helper–free Adenovirus Type–5 Vectors," in *Eukaryotic Viral Vectors,* Gluzman, Y., ed., Cold Spring Harbor Laboratory, Cold Spring Harbor, NY, pp. 187–192 (1982).

Graham, F. L. et al., "Characteristics of a Human Cell Line Transformed by DNA from Human Adenovirus Type 5," *J. gen. Virol. 36:*59–72, Cambridge University Press (1977).

Grubb, B.R., et al., "Inefficient gene transfer by adenovirus vector to cystic fibrosis airway epithelia of mice and humans," *Nature 371:*802–806, Macmillan Publishers Ltd (1994).

Hardy, S., et al., "Construction of Adenovirus Vectors through Cre–lox Recombination," *J. Virol. 71:*1842–1849, American Society for Microbiology (1997).

Havenga, M.J.E., et al., "Second gene expression in bicistronic constructs using short synthetic intercistrons and viral IRES sequences," *Gene 222:*319–327, Elsevier Science B.V. (Nov., 1998).

Hay, R.T., et al., "Replication of Adenovirus Mini–chromosomes," *J. Mol. Biol. 175:*493–510, Academic Press (1984).

He, T.–C., et al., "A simplified system for generating recombinant adenoviruses," *Proc. Natl. Acad. Sci. USA 95:*2509–2514, The National Academy of Sciences of the USA (Mar., 1998).

Hess, M., et al., "The Avian Adenovirus Penton: Two Fibres and One Base," *J. Mol. Biol. 252:*379–385, Academic Press (1995).

Horwitz, M.S., "Adenoviruses," in *Fields Virology,* Third Edition, Fields, B.N., et al., eds., Lippincott–Raven Publishers, Philadelphia, PA, pp. 2149–2171 (1996).

Hunt, C. and Morimoto, R.I., "Conserved features of eukaryotic hsp70 genes revealed by comparison with the nucleotide sequence of human hsp70," *Proc. Natl. Acad. Sci. USA 82:*6455–6459, The National Academy of Sciences of the USA (1985).

Imler, J.–L., et al., "An efficient procedure to select and recover recombinant adenovirus vectors," *Gene Ther. 2:*263–268, Stockton Press (1995).

Karlsson, S., et al., "Transfer of genes into hematopoietic cells using recombinant DNA viruses," *Proc. Natl. Acad. Sci. USA 82:*158–162, The National Academy of Sciences of the USA (1985).

Kawaguchi, T., et al., "Establishment and Characterization of a Chicken Hepatocellular Carcinoma Cell Line, LMH," *Cancer Res. 47:*4460–4464, American Association for Cancer Research (1987).

Khatri, A., et al., "Gene Expression by Atypical Recombinant Ovine Adenovirus Vectors during Abortive Infection of Human and Animal Cells in Vitro," *Virol. 239:*226–237, Academic Press (1997).

Klonjkowski, B., et al., "A Recombinant E1–Deleted Canine Adenoviral Vector Capable of Transduction and Expression of a Transgene in Human–Derived Cells and In Vivo," *Human Gene Ther. 8:*2103–2115, Mary Ann Liebert, Inc. (1997).

Kovesdi, I., et al., "Adenoviral vectors for gene transfer," *Curr. Opin. Biotechnol. 8:*583–589, Current Biology Ltd (1997).

Kumar–Singh, R., and Chamberlain, J.S., "Encapsidated adenovirus minichromosomes allow delivery and expression of a 14 kb dystrophin cDNA to muscle cells," *Human Mol. Genet. 5:*913–921, Oxford University Press (1996).

Lasher, H.N., and Davis, V.S., "History of Infectious Bursal Disease in the U.S.A.–The First Two Decades," *Avian Diseases 41:*11–19, The American Association of Avian Pathologists (1997).

Laver, W.G., et al., "Purification and Properties of Chick Embryo Lethal Orphan Virus (an Avian Adenovirus)," *Virol. 45:*598–614, Academic Press (1971).

Lemay, P., et al., "Human Adenovirus Type 2 Protein IIIa," *Virol. 101:*131–143, Academic Press (1980).

Levenson, V.V., et al., "Internal Ribosomal Entry Site–Containing Retroviral Vectors with Green Fluorescent Protein and Drug Resistance Markers," *Human Gene Ther. 9:*1233–1236, Mary Ann Liebert, Inc. (May, 1998).

Li, P., et al., "The Structural Proteins of Chick Embryo Lethal Orphan Virus (Fowl Adenovirus Type 1)," *J. Gen. Virol. 65:*1803–1815, Society for General Microbiology (1984).

Li, P., et al., "DNA–binding Proteins of Chick Embryo Lethal Orphan Virus: Lack of Complementation between Early Proteins of Avian and Human Adenoviruses," *J. Gen. Virol. 65:*1817–1825, Society for General Microbiology (1984).

Li, P., et al., "Structural Organization and Polypeptide Composition of the Avian Adenovirus Core," *J. Virol. 52:*638–649, American Society for Microbiology (1984).

Li, X., et al., "Dicistronic LacZ and Alkaline Phosphatase Reporter Constructs Permit Simultaneous Histological Analysis of Expression from Multiple Transgenes," *Bio-Techniques 23:*874–882, Clontech Laboratories, Inc. (1997).

Lieber, A., et al., "Recombinant Adenoviruses with Large Deletions Generated by Cre–Mediated Excision Exhibit Different Biological Properties Compared with First–Generation Vectors In Vitro and In Vivo," *J. Virol.* 70:8944–8960, American Society for Microbiology (1996).

Lillehoj, H.S., and Trout, J.M., "Avian Gut–Associated Lymphoid Tissues and Intestinal Immune Responses to Eimeria Parasites," *Clin. Microbiol. Rev.* 9:349–360, American Society for Microbiology (1996).

Lubeck, M.D., et al., "Long–term protection of chimpanzees against high–dose HIV–1 challenge induced by immunization," *Nature Med.* 3:651–658, Nature America Inc. (1997).

McFerran, J.B. and B. McC. Adair, "Avian Adenoviruses—A Review, " *Avian Pathol.* 6:189–217, World Veterinary Poultry Association (1977).

Nichou, A.–I. et al., "Mutational Analysis of the Avian Adenovirus CELO, Which Provides a Basis for Gene Delivery Vectors," *J. Virol.* 73:1399–1410, American Society for Microbiology (Feb., 1999).

Mittal, S.K., et al., "Development of a bovine adenovirus type 3–based expression vector," *J. Gen. Virol.* 76:93–102, Society for General Microbiology (1995).

Miyake, S., et al., "Efficient generation of recombinant adenoviruses using adenovirus DNA–terminal protein complex and a cosmid bearing the full–length virus genome," *Proc. Natl. Acad. Sci. USA* 93:1320–1324, The National Academy of Sciences of the USA (1996).

Ohtsuka K., "Cloning of a cDNA for Heat–Shock Protein hsp40, a Human Homologue of Bacteial DnaJ," *Biochem. Biophys. Res. Commun.* 197:235–240, Academic Press (1993).

Oliner, J.D., et al., "In vivo cloning of PCR products in *E. coli*," *Nucl. Acids Res.* 21:5192–5197, Oxford University Press (1993).

Parks, R.J., et al., "A helper–dependent adenovirus vector system: Removal of helper virus by Cre–mediated excision of the viral packaging signal," *Proc. Natl. Acad. Sci. USA* 93:13565–13570, The National Academy of Sciences of the USA (1996).

Pettersson, U., and Roberts, R.J., "Adenovirus Gene Expression and Replication: A Historical Review," in *DNA Tumor Viruses*, Cold Spring Harbor Laboratory, Cold Spring Harbor, NY, pp. 37–57 (1986).

Plank, C., et al., "Gene Transfer into Hepatocytes Using Asialoglycoprotein Receptor Mediated Endocytosis of DNA Complexed with an Artificial Tetra–Antennary Galactose Ligand," *Bioconjugate Chem.* 3:533–539, American Chemical Society (1992).

Polyak, K., et al., "A model of p53–induced apoptosis," *Nature* 389:300–305, Macmillian Publishers Ltd (1997).

Robbins, A.K., et al., "Characterization of a Pseudorabies Virus Glycoprotein Gene with Homology to Herpes Simplex Virus Type 1 and Type 2 Glycoprotein C," *J. Virol.* 58:339–347, American Society for Microbiology (1986).

Robinson, A.J. et al., "A Circular DNA–Protein Complex from Adenoviruses," *Virol.* 56:54–69, Academic Press (1973).

Schaack, J., et al., "Efficient Selection of Recombinant Adenoviruses by Vectors That Express β–Galactosidase," *J. Virol.* 69:3920–3923, American Society for Microbiology (1995).

Schreurs, C., et al., "Glycoprotein gIII of Pseudorabies Virus Is Multifunctional," *J. Virol.* 62:2251–2257, American Society for Microbiology (1988).

Shenk, T., "Group C Adenoviruses as Vectors for Gene Therapy," in *Viral Vectors: Gene Therapy and Neuroscience Applications,* Kaplitt, M.G. and Loewy, A.D., eds., Academic Press, San Diego, CA, pp. 43–54 (1995).

Shenk, T., "Adenoviridae: The Viruses and Their Replication," in *Fields Virology,* Third Eidtion, Fields, B.N., et al., eds., Lippincott–Raven Publishers, Philadelphia, PA, pp. 2111–2148 (1996).

Shirley, M.W., "Research on Avian Coccidia: An Update," *Br. Vet. J.* 148:479–499, Bailliere Tindall (1992).

Soberon, X., et al., "Construction and Characterization of New Cloning Vehicles: IV. Deletion Derivatives of pBR322 and pBR325," *Gene* 9:287–305, Elsevier/North Holland Biomedical Press (1980).

Stratford–Perricaudet, L.D. et al., "Widespread Long–term Gene Transfer to Mouse Skeletal Muscles and Heart," *J. Clin. Invest.* 90:626–630, The American Society for Clinical Investigations, Inc. (1992).

Talsma, H., et al., "Stabilization of gene delivery systems by freeze–drying," *Int. J. Pharmaceutics* 157:233–238, Elsevier Science B.V. (1997).

Taylor, M.A., and Catchpole, J., "Coccidiosis of domestic ruminants," *Appl. Parasitol.* 35:73–86, Gustav Fischer Verlag Jena (1994).

Van Doren, K., et al., "Infection of Eucaryotic Cells by Helper–Independent Recombinant Adenoviruses: Early Region 1 Is Not Obligatory for Integration of Viral DNA," *J. Virol.* 50:606–614, American Society for Microbiology (1984).

Vermeulen, A.N., "Progress in recombinant vaccine development against coccidiosis. A review and prospects into the new millennium," *Intl. J. Parasitol.* 28:1121–1130, Elsevier Science Ltd (Jul., 1998).

Vrati, S., et al., "Construction and Transfection of Ovine Adenovirus Genomic Clones to Rescue Modified Viruses," *Virol.* 220:200–203, Academic Press (1996).

Weiss, R.S., et al., "Human Adenovirus Early Region 4 Open Reading Frame 1 Genes Encode Growth–Transforming Proteins That May Be Distantly Related to dUTP Pyrophosphatase Enzymes," *J. Virol.* 71:1857–1870, American Society for Microbiology (1997).

Wilson, C., and Kay, M.A., "Immunomodulation to enhance gene therapy," *Nature Med.* 1:887–889, Nature America Inc. (1995).

Xu, Z.Z., et al., "Construction of Ovine Adenovirus Recombinants by Gene Insertion or Deletion of Related Terminal Region Sequences," *Virol.* 230:62–71, Academic Press (1997).

Yates, V.J., and Fry, D.E. "Observations on a Chicken Embryo Lethal Orphan (CELO) Virus," *Am. J. Vet. Res.* 18:657–660, American Veterinary Medical Association (1957).

Zabner, J., et al., "Adenovirus–Mediated Gene Transfer to Ciliated Airway Epithelia Requires Prolonged Incubation Time," *J. Virol.* 70:6994–7003, American Society for Microbiology (1996).

Zabner, J., et al., "Lack of High Affinity Fiber Receptor Activity Explains the Resistance of Ciliated Airway Epithelia to Adenovirus Infection," *J. Clin. Investig.* 100:1144–1149, The American Society for Clinical Investigations, Inc. (1997).

Zheng, B., et al., "The E1 sequence of bovine adenovirus type 3 and complementation of human adenovirus type 5 E1A function in bovine cells," *Virus Res.* 31:163–186, Elsevier Science B.V. (1994).

Co–Pending U.S. Patent Application No. 09/171,461, Baker et al., §102(e) Date: Jan. 12, 1999.

Co–Pending U.S. Patent Application No. 09/399,778, Cotten et al., filed Sep. 21, 1999.

English Language Translation of Document AL1, WO 97/40180.

Co–Pending U.S. Patent Application No. 08/750,180, Cotten et al., §102(e) Date: Feb. 14, 1997.

* cited by examiner

RECOMBINANT, REPLICATION DEFECTIVE CELO VIRUS AND CELO VIRUS DNA

The present application claims the benefit of EP 99 120 358.9, filed Oct. 13, 1999, which is herein incorporated by reference, and U.S. Appl. No. 60/167,770, filed Nov. 29, 1999, which is herein incorporated by reference.

The present invention relates to viral vectors and viral DNA.

Adenovirus has been studied for its role in human disease (25), as a model for many important discoveries in molecular biology, including mRNA splicing, DNA replication, transcription and cell transformation (reviewed in 44) and more recently as a powerful reagent for transient gene expression (12, 46). A detailed understanding of the adenoviral life cycle is well established (reviewed in 50). Since the initial efforts to use adenovirus as a gene transfer vector (18, 52, 28) the virus has gained in popularity as a vector and a number of methods of generating alterations in the viral genome to carry novel genes have been developed (2, 5, 11, 15, 21, 23, 26, 32, 38, 41, 43, 48 reviewed in 31, 49). Because of the ease of vector construction and purification, and because these vectors have a potent ability to transiently transduce novel genetic material into a variety of mammalian cell types in vivo, adenovirus vectors were used extensively in early efforts at clinical gene therapy.

Unfortunately, several features of the adenovirus type 5 (Ad5) based vectors initially used have limited the success in the initial applications. These included both the host immune response to adenovirus (reviewed in ref. 55) as well as the failure of the virus to efficiently enter certain target cell types (20, 58, 59). Thus, there is now an interest in adenovirus types that could provoke less aggressive host immune responses and could enter target cells with greater efficiency.

A large number of alternate adenovirus serotypes are known and may provide advantages in some applications over Ad5-based vectors. Additional adenoviruses that have recently been modified as vectors include the ovine adenovirus 287 (29, 53, 56,), the bovine adenovirus type 3 (40, 60), and the canine adenovirus (30). It was considered that these alternate serotypes would provide both a novel vector backbone to which there is no pre-existing immune response in the target host. Furthermore, because adenoviruses are extremely species specific in their replication capacity (50) a degree of security against inappropriate vector replication is gained by using an vector derived from a distant species of adenovirus.

There are several justifications for pursuing these alternate viral subtypes. For vaccine applications in their non-human hosts, these viruses, if properly modified, may provoke more effective immune responses than a human adenovirus based vector. Furthermore, more robust immune responses might be expected from a replication competent virus; thus a vector is most useful in a host where replication is partially or fully permissive. This is not the case with human adenovirus based vectors in nearly all nonhuman hosts.

It has been an object of the invention to provide an alternative adenovirus vector for use as a gene delivery vector and for use as a vaccine.

To solve the problem underlying the present invention, the avian adenovirus CELO has been chosen to be modified. CELO (chicken embryo lethal orphan or fowl adenovirus type 1, reviewed in 39) was characterized as an infectious agent in 1957 (57). There are few serious health or economic consequences of CELO virus infection. CELO can be isolated from healthy chickens and in general, do not cause disease when experimentally re-introduced into chickens (10).

CELO virus is structurally similar to the mammalian adenoviruses (mastadenoviruses) with an icosahedral capsid of 70–80 nm made up of hexon and penton structures (33); the CELO virus genome is a linear, double-stranded DNA molecule with the DNA condensed within the virion by virus-encoded core proteins (33, 36). CELO virus has a larger genome than Ad5 (44 kb vs. ca. 36 kb, ref. 6, WO 97/40180). The CELO virion has two fibers of different lengths at each vertex (24, 33, 35) rather than the single fiber of most other serotypes (reviewed in 50). The CELO virus is not able to complement the E1A functions of Ad5 and CELO virus replication is not facilitated by Ad5 E1 activity (37). The complete DNA sequence of CELO (6, WO 97/40180) revealed additional differences between CELO virus and the mastadenoviruses including the absence of sequences corresponding to the Ad5 early regions E1A, E1B, E3 and E4. The CELO genome contains approximately 5 kb of sequence at the left end and 12 kb at the right end, rich in open reading frames, which have no sequence homology to Ad5 but probably encode the early functions of the virus.

When developing CELO into a gene delivery vector, it has been considered that the virus is naturally defective in mammalian cells and this property should limit the possibility of complementation by wildtype mammalian adenovirus. The CELO virion has increased DNA packaging capacity and much greater physical stability than the virion of Ad5. One practical feature of CELO is the ability to grow the virus in chicken embryos, a system of low cost and high convenience (9, 33).

For application in avian systems, especially for vaccine applications, it would be useful to have a CELO derivative with reduced replication capacity. Such a replication defective virus would allow transduction of avian species or avian cells similar to replication competent CELO vectors, but the amplification and spread of the modified virus would be limited by the impaired replication capacity of the virus.

A gene termed Gam1 was originally identified in the CELO genome in a search for viral genes that influence cell survival (7). The Gam1 protein is encoded by CELO nucleotides 37391–38239, transcriptional control sequences are located within ca. 1500 basepairs upstream and ca. 300 basepairs downstream of the coding region.

The present invention relates to recombinant CELO virus or CELO virus DNA that have the region spanning nucleotides 37391–39239 of the CELO wild type virus genome completely or partially deleted or altered or that contain an insertion in this region, any of which modifications results in a complete loss of Gam1 expression or prevents the expression of a functional Gam1 protein. Alternately to a disruption in the region defined above, the virus may contain a disruption in the transcriptional control elements of the Gam1 gene. (For simplicity, any modification that results in a complete loss of Gam1 expression or an inhibition of functional Gam1 expression will be referred to "Gam1 disruption" in the following.)

The suitability of a CELO mutation for obtaining a virus of the invention can be readily determined by ascertaining the absence of Gam1 expression. Suitable tests employ standard immunological methods, e.g. immunofluorescence microscopy or Western immunoblotting using antisera specific for the Gam1 protein.

The CELO nucleotide sequence numbering used in the present invention is derived from reference 6, WO 97/40180 and GenBank U46933, which describe the sequence of the wild type CELO virus genome.

CELO virus or CELO virus DNA with Gam1 disruptions, and their derivatives respectively, have been designated CELO AIM65 or CELO AIM65 derivatives, respectively.

In an embodiment, the invention is directed to a CELO AIM65 derivative with a complete or partial deletion and/or insertion within the Gam1 gene as defined above.

Preferably, the nucleotides 37391–39239 are completely deleted to provide more space for inserting the foreign DNA in place of the deletion.

In another preferred embodiment, the deletion comprises the region defined by the rescriction sites SmaI/Bgl II, i.e. the region spanning nt 36818–37972, which removes part of the Gam1 open reading frame.

The deletions defining CELO AIM65 may be combined with mutations defining CELO AIM46 (79) or its derivatives. Examples for AIM46 mutations are complete or partial deletion(s) of the regions spanning nt 41731–43684, 41523–43684, 41002–43684 or 40065–43684. Besides, the CELO AIM65 modifications may also be combined with the modifications described for AIM69 and/or AIM70 (79).

Thus, the CELO virus and CELO virus DNA of the invention carry a Gam1 disruption that is optionally combined with a deletion spanning approximately the region from nt 40,000 to approximately within 200 bp of the right terminus of the virus genome. The region that may be completely or partially deleted or disrupted is thus defined by the last three rightward open reading frames encoding peptides of greater than 99 amino acid residues, with the terminal repeat function of the virus normally residing within the last 100–200 bp of the virus genome remaining undisrupted. Optionally, the CELO virus and CELO virus DNA of the invention may, in addition, have a deletion in the region defined by the open reading for the CELO dUTPase (794–1330). Since CELO AIM65 and its derivatives defined above allow the insertion of large pieces of foreign DNA, they are useful as starting material for producing CELO virus vectors.

Apart from allowing the insertion of an expression cassette for genes, the recombinant CELO virus of the invention has been shown to be replication defective in cell culture.

It was a further object of the invention to provide a method for cultivation of the CELO AIM65 virus of the invention.

The disruption in the Gam1 gene renders CELO AIM65 extensively defective in replication. A study of the biological function of the Gam1 gene revealed that Gam1 expression leads to increases in the cellular levels of certain heat shock proteins. It was therefore hypothesized that an essential function of Gam1 is to upregulate a heat shock response during infection. Based on this hypothesis, it was tested whether heat shock applied to the infected cell could allow the replication of a CELO derivative lacking the Gam1 gene.

Surprisingly it was found that, although the Gam1 deletion severely impaired CELO virus replication, the functions of the Gam1 gene in virus replication could be provided by exposing the host cells to a heat shock. This novel type of complementation allows to grow viruses that otherwise are severely defective in their replication capacity.

The invention relates, in a further aspect, to a method for producing CELO AIM65.

The method comprises the following steps: Cells which support wildtype CELO replication (e.g. LMH cells, ATCC No. CRL-2117) are grown and exposed to a heat shock either before, simultaneously, or after infection with the CELO AIM65 (e.g. 10–1000 particles per cell). Under conditions suitable for cell cultivation and for a period of time sufficient for producing the desired number of viruses, e.g. after cultivation for 4 days at 37° C., lysates of the cells are prepared and virus is prepared by standard methods. The heat shock treatment preferably comprises exposure to temperatures above 43° C., preferably 45° C., for period of time sufficient to complement the replication defect, preferably for 30–120 minutes, most preferably 90 minutes. The optimal conditions can be determined empirically in a routine series of virus growth experiments.

Furthermore, in vivo, in chicken embryos the recombinant CELO virus of the invention is highly defective for replication, i.e. the virus does not replicate when infected at levels below $10^7$ particles per embryo, however when infected at higher multiplicities, wild type levels of the virus can be obtained. This property facilitates the growth of the defective virus for various applications.

Although replication deficient, the virus of the invention, when used at high multiplicities of infection in chicken embryos, grows to wildtype levels and forms, as the virus grown in cell culture under heat shock conditions, the basis of a replication-defective vaccine strain.

Since CELO AIM65 and its derivatives contain the same capsid components as CELO AIM46, CELO AIM65 and its derivatives possess the same ability as CELO AIM46 to introduce genes into a broad range of cell types including, in addition to avian cells, human, bovine, equine, monkey, murine, and canine cell types.

The cells that support CELO virus replication and are thus useful for CELO virus production, may be selected from immortalized cells like LMH (27) or from primary avian embryonic cells, in particular kidney or liver cells. To identify useful cell lines, cells are tested for infectability and the ability to amplify an inoculum of virus after heat shock of the host cell as described below.

Alternatively, once a sufficient stock of the defective virus is obtained from cell culture growth using the heat shock step, the recombinant CELO virus may be produced by introducing CELO virus into chicken embryos at sufficiently high multiplicities (i.e. greater than $10^7$ particles per embryo).

An alternate method of growing CELO AIM65 or its derivatives is based on the observation that Gam1 functions can be partially replaced by overexpressing hsp40 or another gene upregulated by Gam1 in the host cell. Thus replication of AIM65 or derivatives can be obtained by coinfecting the host cells with a recombinant adenovirus directing the synthesis of hsp40 (e.g. Adhsp40) or by transfecting the host cell with a plasmid encoding hsp40. Alternately, the hsp40 expression can be directed by an hsp40 expression cassette inserted directly in the CELO AIM65 genome (e.g. CELOdGhsp40).

In order to produce recombinant a CELO virus genome with a Gam1 disruption, a plasmid bearing the genomic right end 13.3 kb fragment is modified to delete a portion of the Gam1 coding sequence and an expression cassette, e.g. a BamH1 CMV/luciferase/βglobin expression cassette is inserted by standard ligation cloning. This modifed region is built into a recombinant CELO genome by homologous recombination to produce a plasmid (designated pAIM65). This modified CELO genome is then released from the plasmid backbone by restriction digest and introduced by transfection into cells that support CELO virus replication. Useful levels of CELO AIM65 virus replication were found to occur only when using heat-shocked LMH cells.

Alternatively, recombination can be performed in avian cells that support AIM65 viral replication, e.g. heat shocked LMH cells, by introducing a modified CELO subfragment that contains a deletion/insertion with a second CELO fragment such that overlapping homology between the two fragments allows recombination to full length CELO genome bearing the desired deletion/insertion.

The replication defective vectors of the invention have vaccine applications in avian species where wildtype levels of CELO viral replication could produce unwanted toxicity or pathology. The ability to propagate AIM65 derived vectors in inexpensive chicken embryos when inoculated in sufficient quantities or by applying appropriate heat shock conditions (which can be determined by routine cultivation assays), facilitates production of large quantities of the vector for any of these applications.

For vaccine applications, the foreign DNA encodes one or more antigens eliciting an immune response in the individual. The antigen may be the natural protein derived from the pathogen, or an immunogenic fragment thereof, e.g. an immunogenic peptide.

To drive expression of the foreign DNA, an expression cassette can be used, which typically includes a promoter active in the target cells, the cDNA of interest, a polyadenylation signal and optionally an intron. Alternately, the DNA inserted into the modified CELO genome may include endogenous CELO promoters, introns and polyadenylation signals to drive expression of the cDNA of interest.

An example for a useful expression cassette, which can be prepared by conventional methods, is derived from a plasmid designated pPM7. It contains the Cytomegalovirus (CMV) immediate early enhancer/promoter followed by a short polylinker with PacI, HpaI and KpnI sites, followed by a rabbit β-globin intron/polyadenylation signal. The CMV/β-globin material may be derived from plasmids available in the art (e.g. from the plasmid pLuc (74), which carries the luciferase gene), modified by PCR to add flanking restriction sites, e.g. BamH1, and subsequently modified by homologous recombination to replace the luciferase cDNA with a PacI/HpaI/KpnI polylinker. The final BamH1 cassette can be cloned into pSP65 to generate pPM7. cDNAs to be cloned into CELO AIM65 derivatives are first cloned into pPM7 using the unique restriction sites (PacI/HpaI/KpnI). Subsequently a restriction or PCR fragment, e.g. a BamH1 fragment, is prepared containing the CMV promoter/cDNA/β-globin unit which is introduced into PacI linearized pAIM65 by homologous recombination. The CMV and βglobin sequences provide homology for the recombination and the luciferase cDNA is thus replaced with the novel cDNA of interest.

The expression cassettes described above can be modified, e.g. by using, instead of the CMV enhancer/promoter, a variety of other viral or cellular promoters including, but not limited to the SV40 enhancer promoter, the Rous Sarcoma Virus long terminal repeat (RSV LTR), the human β-actin promoter, the CELO virus major late promoter, the adenovirus major late promoter, the rat insulin promoter.

Alternatives to to the rabbit β-globins intron/polyadenylation signal include, but are not limited to the intron/polyadenylation signals from SV40, introns and polyadenylation signals from other viruses and from cellular genes could also be used.

Alternatively to using an expression cassette, the foreign cDNA may be a simple insert within a region defining CELO AIM 46 or the deoxyUTPase, thus using endogenous CELO regulatory sequences, e.g promotor, intron, polyadenylation signal.

In the case that two different foreign cDNAs are to be expressed from the CELO vector, e.g. cDNAs encoding two different antigens from a pathogen, the following strategies may be used: in a first embodiment, two gene expression cassettes (carrying different cDNAs and different regulatory sequences) can be inserted into the CELO genome. Alternately, an internal ribosome entry site (IRES) can be used to provide expression from two cDNAs using a single promoter, as described by e.g. 70; 67; 71; 72. Thus, a typical expression cassette for CELO AIM65 carrying two cDNAs to be expressed, includes a promoter, the first cDNA, an IRES, and the second cDNA followed by an optional intron and by a polyadenylation signal.

The foreign cDNA, e.g. antigen cDNA, can be isolated from the genomes of the pathogens by standard methods, e.g. by PCR or by restriction digest, optionally including reverse transcription to convert RNA to DNA, and introduced into a transfer vector carrying the regulatory sequences and unique restriction sites, e.g. the pPM7. Subsequently, this antigen expression unit a recombined into a linearized plasmid bearing the CELO genome and having the same regulatory sequences and corresponding restriction sites, e.g the plasmid pAIM65. The resulting CELO-AIM65 vector, carrying the antigen cDNA, can be grown and purified from chicken embryos.

Examples for antigens useful for vaccine applications are given in WO 97/40180, which is fully incorporated by reference herewith.

Further examples for antigens that may be carried by the virus for vaccination applications are antigens of the infectious bursal disease virus (IBDV; 64) and antigens of Chicken coccidia, e.g. *Eimeria acervulina, Eimeria brunetti, Eimeria maxima, Eimeria mitis, Eimeria necatrix, Eimeria praecox* and *Eimeria tenella* (61, 62, 63), examples for antigens are a parasite refractile body transhydrogenase, lactate dehydrogenase, Ea1A and EaSC2 (reviewed in 77).

Further examples for antigens are the glycoprotein C (gC, glycoprotein gIII) of the porcine pathogen pseudorabies virus (the causative agent of Aujeszky's disease (75; 76; 69). A CELO AIM46 vector carrying gC can be used to elicit an anti-pseudorabies response in pigs.

A robust immune response is to be expected from a replication competent virus. However, under certain conditions, the replication of CELO derived vectors (e.g AIM46 vectors) may produce unsuitable levels of pathology in the host. Therefore, the replication defective vectors of the current invention may be useful at limiting the spread of the vaccine without compromising the initial entry and gene expression from the vector in the host. In this regard, the CELO vectors of the present invention, CELO AIM65 and its derivatives, are ideally suited for avian vaccine applications.

The recombinant CELO virus vectors of the invention are also useful in human vaccine or gene transfer applications. Wild type CELO is replication defective in mammalian cells, therefore the additional replication block generated by the removal of Gam1 expression provides further measure of security. Furthermore, the removal of Gam1 expression will lower the amount of background gene expression from the vector which may have unpredictable effects on the host cell or organism.

An additional argument for pursuing a non-human adenovirus comes from the experience with human adenovirus in human gene transfer applications. Pre-existing immune responses to human adenovirus can impair the initial transduction by human adenovirus based vectors or might exacerbate the cellular immune response to transduced cells. A patient may have no immune experience with an adenovirus from a distant species (although 2 of 7 patients had neutralizing antibodies to the canine adenovirus vector; 30) and initial transductions will not be compromised by the host response to viral antigens. Except for certain agricultural workers, a previous immune exposure to CELO antigens would not be expected in most of the human population. CELO vectors might therefore have an advantage over vectors based on more common human adenovirus serotypes.

An additional conceptual advantage of CELO based vectors of the invention is that CELO, like the bovine, ovine, and canine adenoviruses, is naturally replication defective in human cells. Thus, replication of these vectors will not occur in human patients even in the presence of a wildtype human adenovirus infection.

For gene therapy applications, the foreign DNA may comprise any one or more DNA molecules encoding a therapeutically active protein. Examples are immunomodulatory proteins like cytokines; receptors, enzymes, proteins effecting apoptosis, proteins modulating angiogenesis, e.g. sFLT, FGF receptors, etc. For tumor vaccine applications, the foreign DNA encodes one or more tumor antigens or fragments thereof, preferably in combination with a cytokine.

Examples for human vaccine applications, gene therapy and tumor vaccine applications are given in WO 97/40180, which is fully incorporated by reference herewith.

For vaccine applications, the vector of the invention may be packaged as an enteric coated dosage unit, or in an injectable form for intramuscular, intraperitoneal or subcutaneous injection. Alternately, the vector may be admistered as a paste or a fluid intranasally or intratracheally, as an aerosol or as an intraocular drop. The vector may also be supplied incorporated in feed pellets or in the drinking water.

The quantity of virus introduced per patient, animal or egg may range from 1 to $10^{12}$ particles.

The virus preparation may include a physiological buffered saline or HEPES buffered saline and may optionally be mixed with adjuvants such as vitamin-E acetate, oil/water emulsion, aluminium hydroxide, -phosphate or -oxide, mineral oil emulsions such as Bayol$^{(R)}$ or Marcol 52$^{(R)}$ and saponins.

It may be useful to use a freeze-dried form of the virus as a vaccine (78). The inclusion of a stabilizer such as 10% sucrose may be used with a controlled two-step drying process (78). Alternative stabilizers include carbohydrates such as sorbitol, mannitol, trehalose, starch, sucrose, dextran or glucose, proteins such as albumin or casein, or their degradation products.

In vaccine applications, in order to enhance the host immune response, the immune response elicited by the application of the CELO vaccine vector that carries a specific antigen, can be boosted by additionally adminstering the same antigen or an immunogenic fragment thereof. Preferably, the additionally administered antigen is recombinant; it can be obtained by standard methods or by the method described below that uses CELO vectors to obtain the recombinant proteins from eggs. The combined application of the vector and the antigen can be performed as described by (65, 73). Preferably, the recombinant antigen is administered, optionally together with an immunostimulating adjuvant, subsequent to the CELO vector.

In a further aspect of the invention, CELO virus is used for producing any protein of interest.

CELO AIM65 derivatives may have advantages over replication-competent CELO virus derivatives in that toxicity produced by the virus replication could limit protein production. Cells or embryos infected with AIM65 derivatives are expected to survive longer than cells or embryos infected with replication competent CELO derivative and thus, the production of recombinant proteins encoded by AIM65 derivatives is expected to be higher.

In this embodiment of the invention, the CELO virus, e.g. CELO AIM65 or its derivatives, is engineered, as described above, by introducing the cDNA or, preferably, an expression cassette, encoding the protein of interest into one of the insertion sites of the recombinant CELO DNA of the invention. Virus may be obtained by replication in suitable cells, as described above, and the recombinant virus is introduced, preferably by injection into the allantoic cavity of an avian embryo. Preferably, approximately $4 \times 10^7$ particles are introduced into the allantoic cavity of 7 to 9 day old chicken embryos, which are subsequently incubated for three to four days at 37° C. The recombinant material is then recovered from the allantoic fluid, serum, yolk, amniotic fluid or from the embryo itself.

The protein of interest may be an intracellular or a secreted protein. In the case of a intracellular protein, the protein can be recovered by lysing infected cells that accumulate in the allantoic fluid. In the case of a secreted protein, the material can be recovered from various extracellular fluids of the embryo (allantoic fluid, amniotic fluid, serum, yolk) or, in analogy to the recovery of intracellular proteins, by lysing infected cells.

In a preferred embodiment, the protein of interest is expressed as a fusion protein comprising the protein and, as a stabilizing sequence, an immunoglobulin Fc domain. The secretion of the recombinant protein can be directed by the natural signal sequence from the protein, which may, in addition to the signalling function, have a stabilizing function. The Fc domain confers stability to the protein in the extracellular space and provides a protein sequence that can be used for affinity purification of the recombinant protein using, for example, Protein A or Protein A/G chromatography resins. Constructs that include an Fc domain for stabilization and are thus useful to be expressed from CELO, have been employed to make soluble forms of the FGF receptor 2 (sFGFr; 66) and the VEGF receptor 1 (sFLT; 68).

As alternatives to the signal sequences of FLT and the FGF receptor, signal sequences from or fusions with the proteins ovalbumin, conalbumin, avidin and lysozyme can be used. These are proteins that are synthesized in the liver and/or oviduct of chickens and accumulate within the egg. Thus, using part or all of the coding sequence of these proteins fused to a protein of interest are expected to yield secreted recombinant proteins that are stable within the developing embryo; furthermore, using sequences of this type, e.g. avidin, provides a tag that facilitates chromatographic purification.

Figure 1:
FIGS. 1A–1C. Demonstration the Gam1 expression elevates heat shock protein levels.
Figure 1:
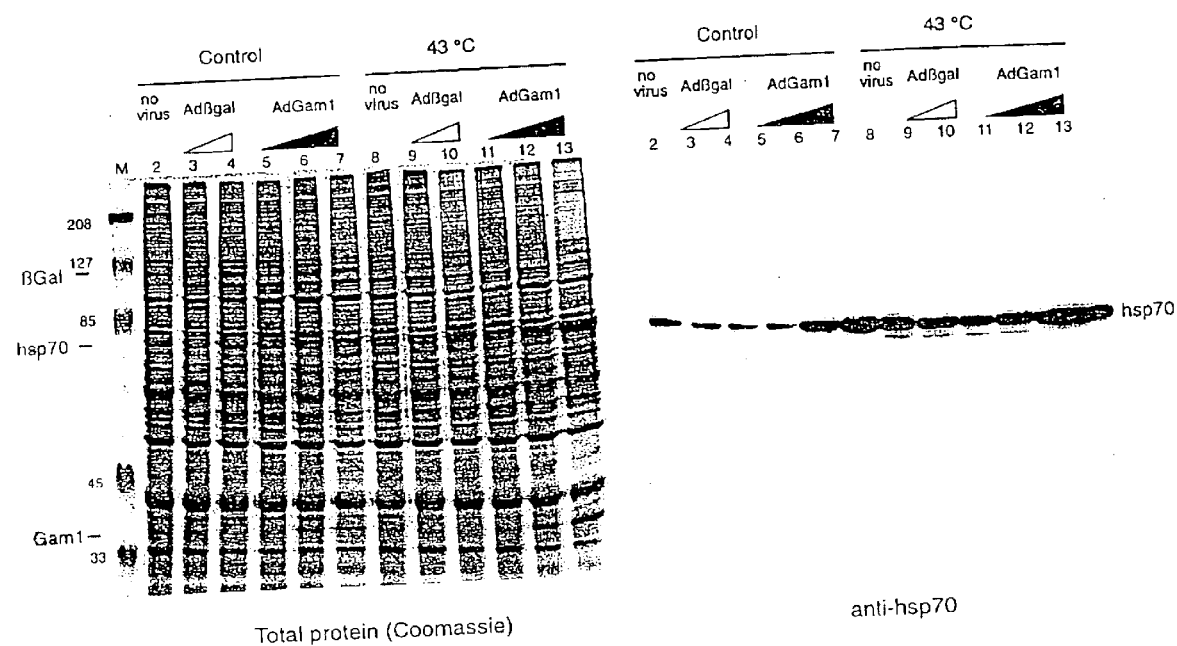
Figure 1:
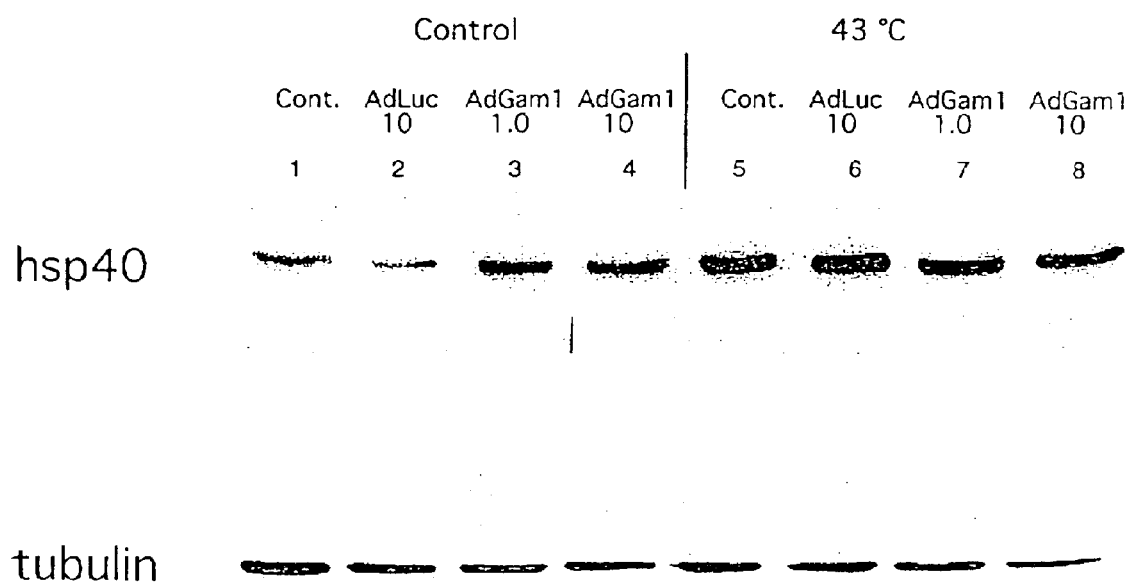

8a: CELO capsid protein production.

8b: Generation of infectious CELO particles.

Unless otherwise stated, the following materials and methods were used in the Examples:

a) Generation of a Recombinant a CELO Virus Genome with a Disrupted Gam1 Gene

In order to produce recombinant a CELO virus genome with a disrupted Gam1 gene, a plasmid bearing the genomic right end 13.3 kb fragment (pB13.3) (the sequence from the Hpa I site at nt 30502 until the right end terminal repeat/ ligated to an SpeI site cloned into pBluescript) was digested with the restriction enzymes BglII and SmaI, and the BamH1 CMV/luciferase/βglobin expression cassette was inserted by standard ligation cloning. This removed the region from nt 36818 to 37972, including the first part (581 bp) of the Gam1 coding sequence and produced the plasmid pAIM55 containing a disrupted Gam1 coding sequence. A MluI, SwaI fragment from pAIM55 was introduced into pW üHpa (digested with XhoI; 79) using homologous recombination in E coli BJ5183 (5, 13) to produce pAIM62, which was subsequently linearized with HpaI and used to recombine with wildtype CELO DNA to produce pAIM65. All manipulations were confirmed by restriction analysis and sequence analysis. The CELO nucleotide sequence numbering is derived from reference 6 and GenBank U46933.

b) Generation of CELO Virus Expressing Luciferase

The luciferase cassette containing the Cytomegalovirus immediate early enhancer/promoter, the luciferase cDNA (14) followed by a rabbit βglobin intron/polyadenylation signal was derived from pCLuc (45), modified by PCR to add flanking BamH1 sites and cloned into pBlueScript II (SK) to generate pBlueLuc. For most of the CELO insertions, the luciferase cassette was isolated from pBlue-Luc by BamH1 digestion and the termini were made blunt by treatment with Klenow enzyme.

c) Generation of Recombinant Type 5 Adenovirus Expressing Gam1

The Gam1 coding sequence (nt 37391–39239 in the CELO genome) plus an amino terminal myc tag were amplifed from pSG9mGam1 (7) and modified to contain terminal Pac1/Kpn1 restriction sites using PCR. The fragment was transferred into an E1/E3 negative adenovirus 5 genome using homologous recombination in bacteria (5, 79). The final virus bears an expression unit containing a CMV promoter, the myc-tagged Gam1 coding sequence and rabbit β-globin intron polyA signal embedded in the E1 region. Control E1-negative Ad5 viruses expressing luciferase (AdLuc), eGFP (AdGFP) or βgalactosidase (AdRSVβgal) and their purification on CsCl gradients have been described previously (79, 80).

d) Generation of Recombinant Adenovirus Type5 and CELO Virus Expressing Human hsp40 or Human hsp70

Adhsp40, Adtethsp70: The hsp40 cDNA was amplified from a human hsp40 cDNA plasmid (Ohtsuka, 1993) using PCR and transferred into an E1/E3 negative adenovirus 5 genome using homologous recombination in bacteria (Chartier et al., 1996; Michou et al., 1999). The final virus bears an expression unit containing a CMV promoter, the hsp40 coding sequence and rabbit β-globin intron polyA signal embedded in the E1 region. Similar methods were used to construct an adenovirus bearing a human hsp70 coding sequence Hunt and Morimoto, 1985).

The CELOdGhsp40 and CELOdGhsp70 genomes were constructed by exchanging the CMV/luciferase/β-globin cassette in pAIM65 for CMV/hsp40/β-globin or CMV/ hsp70/βglobin cassettes.

e) Evaluation of the Recombinant CELO Genomes on LMH Cells and Preparation of Viral Stocks The recombinant CELO plasmids were digested with SpeI to release the viral genome from the plasmid, extracted with phenol, with chloroform and then purified by gel filtration (Pharmacia Nick Column) equilibrated with TE.

Transfection complexes were prepared using a modification of the PEI technique (1, 3, 79). The DNA was condensed with PEI in two steps as follows: PEI MW 2000 (2.5 µl of 10 mM PEI in 125 µl HBS (150 mM NaCl, 20 mM HEPES, pH 7.4)) was added dropwise to 3 µg of DNA diluted in 125 µl of HBS. The sample was incubated at room temperature for 20 minutes. Subsequently, PEI MW 25000 (3.5 µl of 10 mM in 125 µl of HBS) was added dropwise to the sample and the complex incubated at room temperature for an additional 20 minutes.

Figure 2:
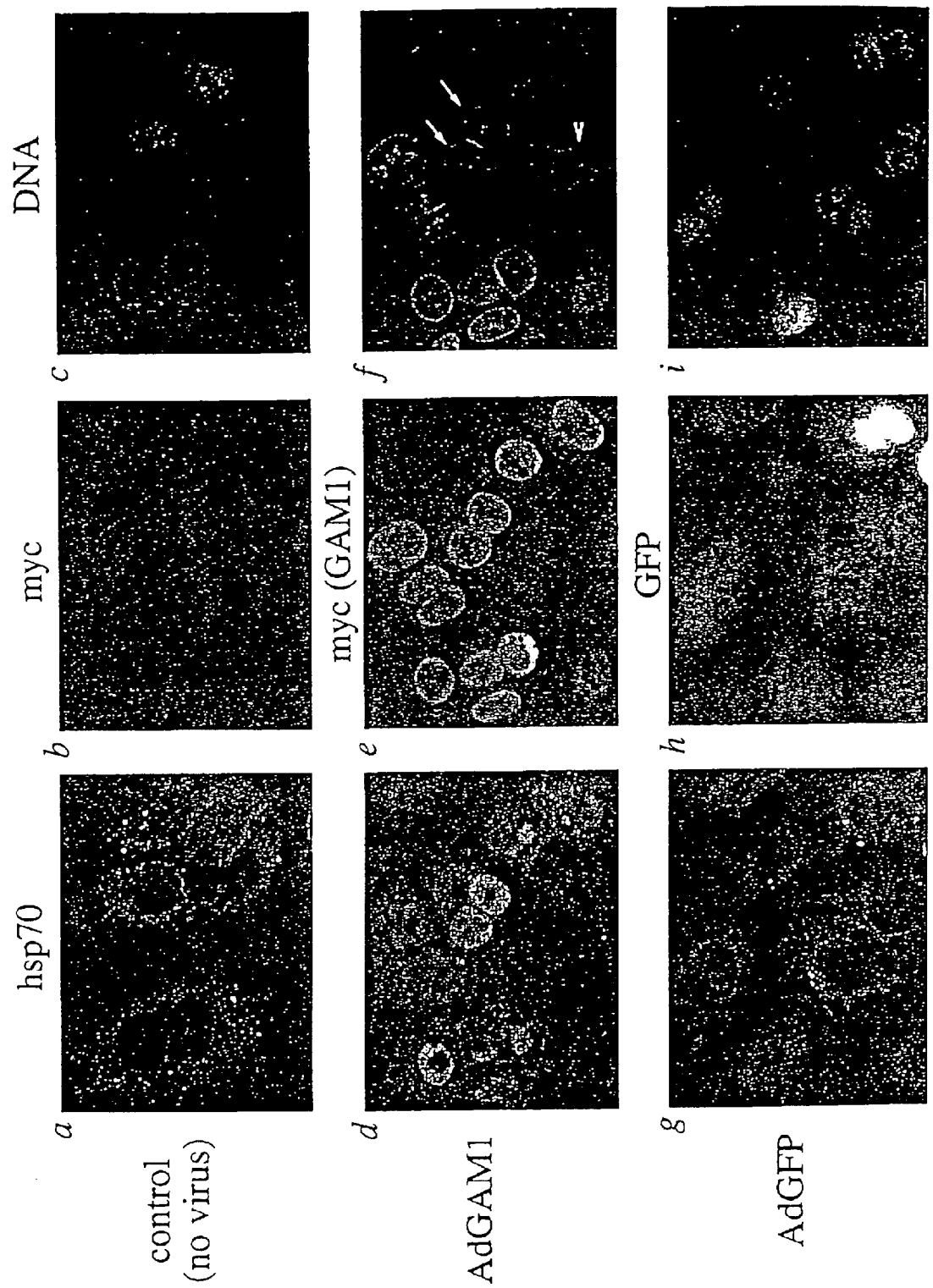
FIG. 2. Gam1 expression relocates hsp70 to the nucleus in the absence of heat.

Leghorn Male Hepatoma (LMH) cells (27) were seeded the day before transfection in 24 wells plates at 7×10$^4$ cells/well (24 well dish). For transfection, the cell culture medium was replaced by 400 µl DMEM. The transfection complex (90 µl per well) was added to the cells for 4 hours at 37° C. after which the medium was replaced with fresh, 10% fetal calf serum containing medium. In one set of samples (indicated by +AdGam1) an aliquot of AdGam1 (1000 particles per cell) was added 24 hours later. After 5 days the cells were harvested and assayed for luciferase activity (=Passage 0). An additional culture was used to infect a fresh set of LMH cultures either alone, or with the addition of AdGam1 as before. Thus, cleared lysates from transfected cells were prepared as follows. Cells plus supernatant were harvested, collected by centrifugation and the cell pellets were resuspended in 2 ml of processed supernatant. The material was frozen and thawed 3 times, sonicated in a bath sonicator to release viral particles, the cell debris was removed by centrifugation, and the cleared lysate used for further amplification on fresh cultures of LMH cells. The harvest, luciferase assay and passage were repeated every 5 days for 5 passages. FIG. 2 left panel: CELO AIM65 (CELOAG) alone; right panel: CELO AIM65 (CELOΔG) plus AdGam1. The luciferase activity (average of three cultures plus standard deviation) is indicated for each passage.

f) Cell Fractionation

Cell pellets were suspended in buffer A and lysed by passage through a 21 ga. needle. Nuclei were harvested by centrifugation (large scale HBS rotor, 20 minutes, 8 K) small scale 5 minutes eppendorf, 10,000×g. The cytoplasmic supernatant (C) was removed and the pellet was gently resuspended in buffer B. The suspension was again centrifuged to yield the supernatant nuclear extract (N1) and the pelleted, extracted nuclei (N2).

Buffer A: 20 mM HEPES, pH 7.4, 0.5 M sucrose, 50 mM NaCl, 1 mM EDTA, 0.25 mM EGTA, 0.5 mM spermidine, 0.15 mM spermine, 0.5% Triton X-100, 7 mM β-mercaptoethanol, protease inhibitor cocktail (Sigma).

Buffer B: 20 mM HEPES, pH 7.4, 25% glycerol, 100 mM NaCl, 0.1 mM EDTA, 0.1 mM EGTA, 0.5 mM spermidine, 0.15 mM spermine, 7 mM β-mercaptoethanol, protease inhibitor cocktail (Sigma).

g) Immunoblotting Analysis

A549 cells were lysed in lysis buffer (150 mM NaCl, 50 mM Tris, pH 7.5, 5 mM EDTA, 1% NP-40 containing protease inhibitor cocktail (Sigma)). Cells were agitated at 4° C. for 30 minutes, passaged through a 25 ga. needle 5 times, sonicated in a bath sonicator for 5 minutes, centrifuged 14,000 RPM (Eppendorf) for 5 minutes and the supernatant was used for immunoblotting analysis. Equal quantities of protein (measured by Bradford reagent, Pierce) were resolved by PAGE, transferred to nitrocellulose and probed with the indicated antiserum preparations (see below). Antibody binding was revealed using the appropriate peroxidase-conjugated secondary antibodies (Dako) and ECL reagents (Amersham).

h) Immunofluorescence

Cells were plated on glass cover slips (12×12 mm) in 6 well dishes 24 hours before infection. Cells were fixed one day after infection in 4% paraformaldehyde for 15 min, rinsed 3 times with PBS, permeabilized with PBS/0.1% Triton X-100 (PBT) for 15 min, blocked in 5% BSA/PBT for 30–60 min, incubated with primary antibody for 15 min in 5% BSA/PBT, washed 3 times with PBT, incubated with secondary antibody for 15 min in 5% BSA/PBT, washed 2 times with PBT, 2 times with PBS and mounted in 50% glycerol/PBS, 10 mM Tris pH 8.5, 4% n-propyl gallate (Sigma); all incubations were done at room temperature. DNA was stained with Hoescht dye. Images were acquired with a cooled CCD camera (Spot II; Diagnostic Instruments) mounted on an Axiovert microscope (Zeiss) and equipped with 63×/1.4 lens; with filters from Chroma Tech. and processed using Adobe Photoshop software.

Antiserum preparations used were a murine monoclonal 9E10 recognizing the myc epitope (81) murine monoclonal, RPN-1197 recognizing hsp70 (Amersham) or goat polyclonal sera recognizing hsp70, hsp40, hsp90a, hsc70 and hsp27 (Santa Cruz Biotechnology), antitubulin (clone DM1A, Sigma) and a rabbit polyclonal directed against total capsid proteins (79). Secondary antibodies were a DTAF conjugated donkey anti mouse, DTAF conjugated donkey anti rabbit, Cy3 conjugated donkey anti goat (Jackson Laboratories), all were used at 1:100 dilutions.

j) Additional Reagents

CELO AIM46 was purified from either LMH cultures or infected chicken embryos as previously described (9, 79).

The LMH cell line (27) was obtained from ATCC No. CRL-2117, the A549 cell line was also obtained from the ATCC No. CCL-185, both cell types were cultured in DMEM/10% FCS.

The 293 cell line (19) was obtained from the ATCC (No. CRL-1573) and was cultured in MEMalpha with 10% newborn calf serum.

EXAMPLE 1

Gam1 expression from a recombinant virus elevates hsp70 and hsp40 levels.

To analyze the cellular response to Gam1, an E1-defective adenovirus type 5 vector expressing a myc epitope tagged Gam1 protein was constructed (AdGam1).

In the experiments shown in FIG. 1a, extracts from A549 cells that were either transfected with a plasmid encoding a myc-tagged E1B 19K gene (lane 1) or myc-tagged Gam1 (lane 2 and 3) or infected with AdGam1 at 300, 3000 or 30,000 particles /cell (lanes 4, 5, 6) were analyzed by immunoblotting using an antibody against the myc epitope (81).

It becomes clear from FIG. 1a that AdGam1 directs substantial levels of Gam1 expression in 80–100% of the cells exposed to the virus (see FIG. 2).

To determine if Gam1 expression influences hsp70 protein levels, A549 cells were infected with either AdGam1 or a control adenovirus encoding nuclear targetted β-galactosidase (Adβgal). In the experiments shown in FIG. 1b, as in FIG. 1a, cells were infected with the indicated adenovirus; heat shock (43° for 90 minutes) was applied as indicated, 24 hours later. Cells were harvested 48 hours post-infection, extracts were prepared, equal quantitites of protein were resolved by SDS-PAGE and either stained with Coomassie blue (left panel) or analyzed by immunoblotting for hsp70 (right panel). Extracts from non-infected cells (lane 2); cells infected with control adenovirus (Adβgal) at 1000 (lanes 3, 9) or 10,000 particles per cell (lanes 4, 10) or with AdGam1 at 100 (lanes 5, 11) 1000 (lanes 6, 12) or 10,000 particles per cell (lanes 7, 13); no heat shock (lanes 2–7); heat shock (lanes 8–13).

Both virus-encoded transgene products were highly expressed (FIG. 1b, left panel). A substantial increase in hsp70 protein was observed in cells expressing Gam1 (FIG. 1b, right panel). No hsp70 induction was observed in cells expressing similar quantities of nuclear targetted βgalactosidase, demonstrating that neither E1-defective adenovirus infection, nor high levels of exogenous protein expression were responsible for the effect. The hsp70 induction was similar to that obtained with heat shock (FIG. 1b, right panel); a modest synergy was observed if both Gam1 expression and heat were applied (compare lanes 5–7 to lanes 11–13).

An analysis of the effects of Gam1 expression on hsp40 levels was performed. In FIG. 1c, the infection, heat shock and immunoblotting was as described in FIG. 1a. Non-infected cells (lanes 1, 5); cells infected with 10,000 particles/cell control adenovirus (AdLuc; lanes 2, 6); cells infected with 1000 particles per cell AdGam1 (lanes 3, 7); cells infected with 10,000 particles/cell AdGam1 (lanes 4, 8); no heat shock (lanes 1–4); heat shock (lanes 5–6). Duplicate blots were probed with antiserum to hsp40 (top panel) or tubulin (bottom panel).

It was found that Gam1 expression also led to a modest increase of hsp40 (FIG. 1c) but not of hsp90α, hsc70, or hsp27 (results not shown in the Figure.).

EXAMPLE 2

Gam1 expression relocates hsp70 to the nucleus in the absence of heat.

It is known that hsp70 moves to the nucleus following heat shock[15,16]. Using immunofluorescence, the cellular localization of hsp70 in cells expressing Gam1 was monitored (FIG. 2a–i).

In the experiments shown in FIG. 2, panels a–i show an immunofluorescence analysis of A549 cells that were non-infected (panels a, b, c); infected with AdGam1 (10,000 particles per cell; panels d, e, f) or with AdGFP (10,000 particles per cell; panels g,h,i), staining with anti-hsp70 (panels a, d and g), staining with anti-myc antibody for myc-tagged Gam1 (panels b, e) or GFP expression (panel h) or staining for DNA (panels c, f and i). In panel f, the arrows indicate cells with high Gam1 expression and nuclear accumulation of hsp70; the arrowhead indicates a cell with no detectable Gam1 expression and no nuclear accumulation of hsp70.

Non-infected A549 cells present a predominantly cytoplasmic hsp70 distribution (FIG. 2a–c). Like heat shock, Gam1 expression causes relocalization of hsp70 to the nucleus (FIG. 2d–f). Infection of cells with a control adenovirus expressing GFP in both cytoplasmic and nuclear compartments causes no change in hsp70 levels or localization (FIG. 2g–i).

EXAMPLE 3

Both Hsp70 and hsp40 localization are influenced by Gam1 expression.

Figure 3:
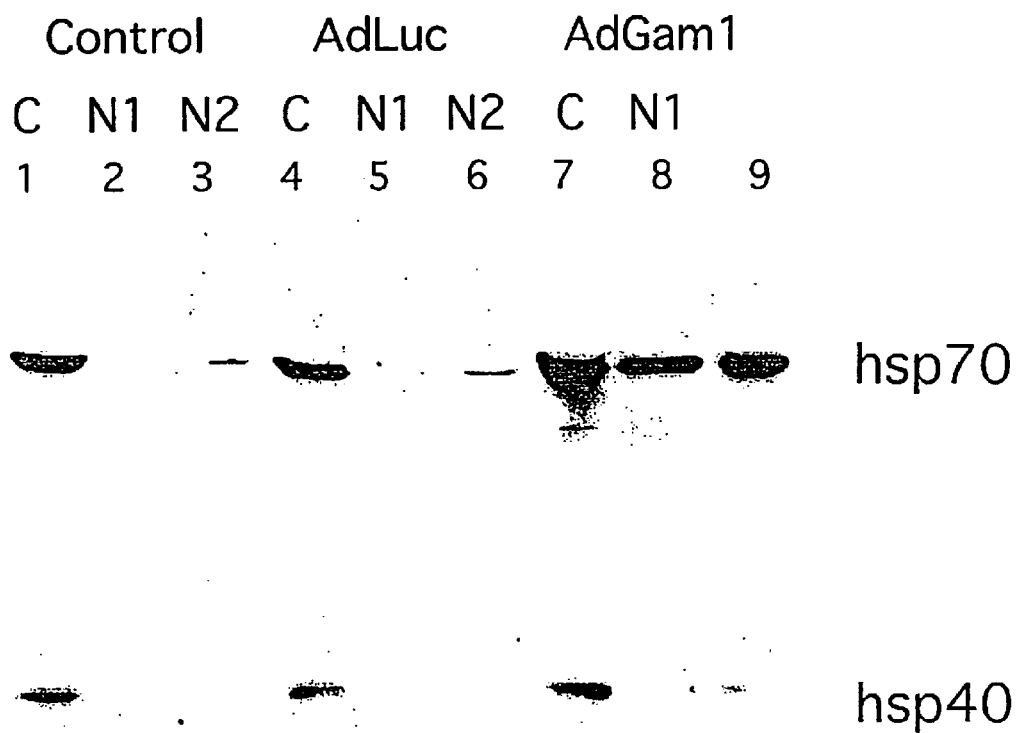
FIG. 3. Analysis of the subcellular localization of hsp70 and hsp40.

FIG. 3 shows an analysis of the subcellular localization of hsp70 and hsp40 in response to Gam1 expression. A549 cells were infected with either a control adenovirus (AdLuc) or AdGam1. Two days after infection cells were lysed, nuclei were harvested by centrifugation and extracted once with a 100 mM NaCl buffer (see Methods). Aliquots of the cytoplasmic fraction (C), 100 mM nuclear extract (N1), and remaining nuclear material (N2) were analyzed by immunoblotting for the presence of hsp70 or hsp40. The Figure shows extracts from non-infected cells (lanes 1–3); from cells infected with control adenovirus (AdLuc) at 10,000 particles per cell (lanes 4–6); and from cells infected with AdGam1 at 10,000 particles per cell (lanes 7–9).

When monitored biochemically, there was an increase in hsp70 and hsp40 levels in the nuclear fractions from AdGam1 infected cells but not from non-infected cells nor from control virus-infected cells, where hsp40 and hsp70 are found almost exclusively in the cytoplasmic fraction (FIG. 3).

EXAMPLE 4

Hsp70 is upregulated during CELO infection.

Figure 4:
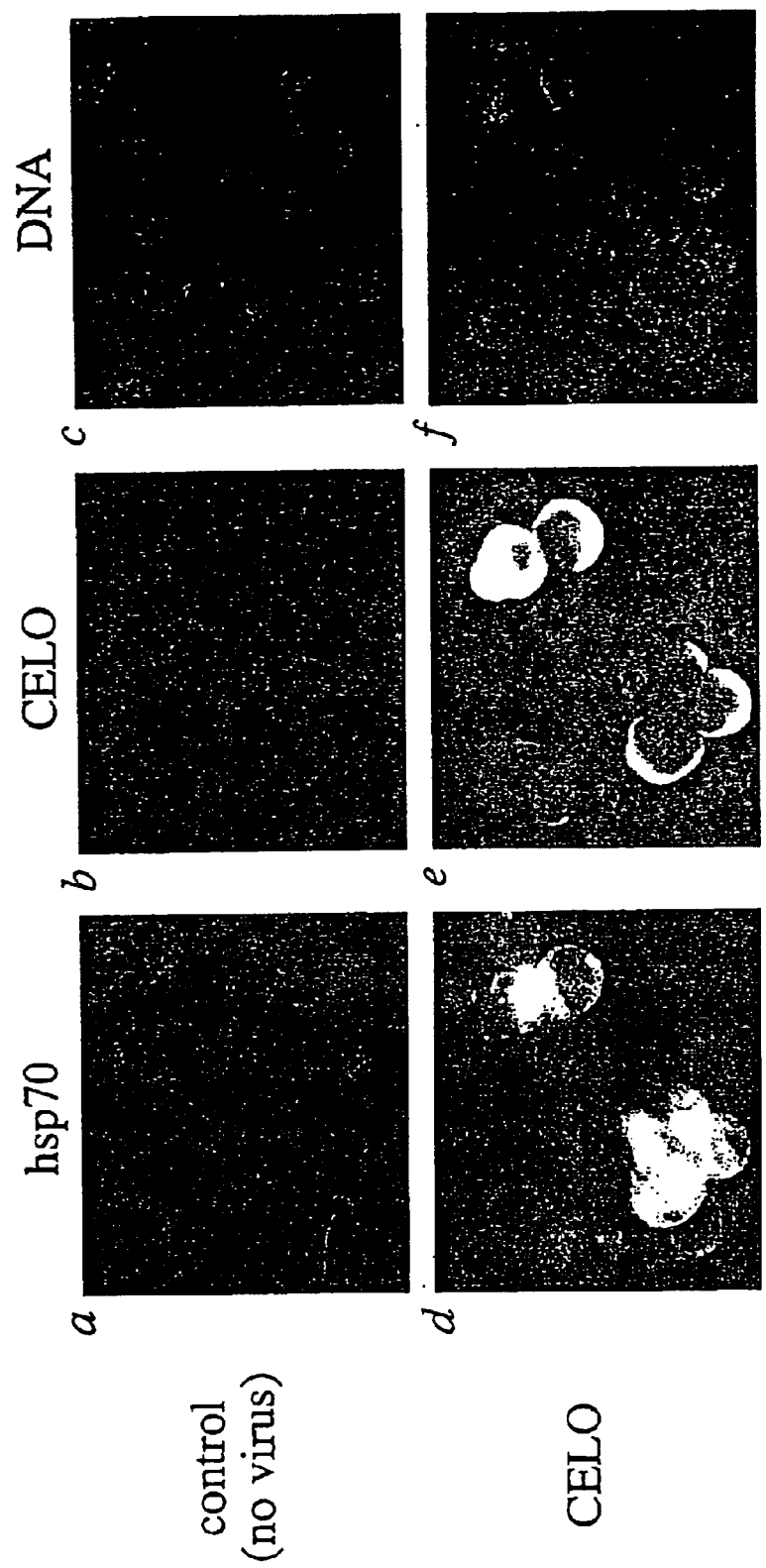
FIG. 4. Hsp70 is upregulated during CELO infection.

It was important to determine if hsp70 induction is part of a normal CELO infection process. FIG. 4 shows an immunofluorescence analysis of hsp70 levels in LMH cells staining with anti-hsp70 (panels a, d), staining with anti-CELO capsid (panels b, e) or staining for DNA (panels c, f). Cells were either noninfected (panels a, b, c) or infected with wild type CELO (100 particles per cell; panels d, e, f).

Hsp70 levels were also found to increase during CELO replication in LMH cells (FIG. 4, compare a and d). The accumulation of hsp70 during infection is nuclear and perinuclear, while CELO capsid proteins appear to accumulate primarily in perinuclear sites (compare d and e).

EXAMPLE 5

Analysis of CELO AIM65 growth and complementation with AdGam1.

To examine the requirement for Gam1 in CELO replication a Gam1-negative CELO bearing a luciferase gene was prepared (CELO AIM65, see methods section) and the replication capacity of the encoded virus was analyzed.

The CELO AIM65 genome was transfected into LMH cells alone, or followed 24 hours later, by infection with 1000 particles per cell of AdGam1. After 5 days the cells were harvested and assayed for luciferase activity. An additional culture was used to infect a fresh set of LMH cultures either alone, or with AdGam1. This harvest, luciferase assay and passage were repeated every 5 days for 5 passages. The left panel shows the results from CELO AIM65 alone; the right panel shows the results from CELO AIM65 plus AdGam1. The luciferase activity (average of three cultures plus standard deviation) is indicated for each passage.

Figure 5:
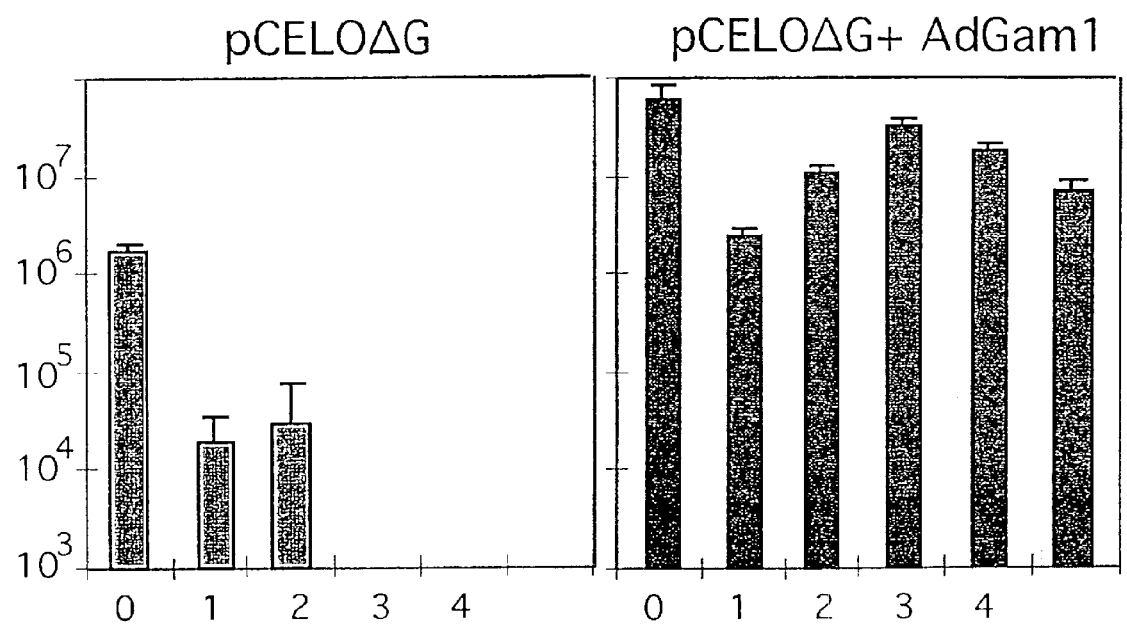
FIG. 5. Analysis of CELO AIM65 growth and complementation with AdGam1.

It becomes clear from the results that after passage 2, luciferase activity from CELO AIM65 is no longer detectable, indicating that virus replication is blocked in the absence of Gam1 (FIG. 5, left panel). However, if Gam1 was supplied from a second virus during the initial transfection and subsequent passages, transduction of luciferase activity was obtained, indicating the production of infectious virus (FIG. 5, right panel). Thus it can be concluded that the Gam1 gene is essential for virus replication and the Gam1 can be supplied from a second, unrelated virus to complement virus replication.

EXAMPLE 6

Analysis of CELO AIM65 growth in chicken embryos.

The replication of CELO AIM65 was also assessed in chicken embryos, the natural site of CELO replication. The indicated particle numbers of either CELO AIM46 or CELO AIM65 were injected into the allantoic cavity of 9 day embryos. After a 4 day incubation at 37° C., the virus present in lysates of allantoic fluid was measured by luciferase transduction in 293 cells. Each value represents the average of at least 5 independent embryo infections with luciferase transduction measured in triplicate for each embryo's allantoic fluid. In independent experiments, CELO AIM46 and CELO AIM65 were found to have equal luciferase transduction activity (per viral particle) in 293 cells with $1 \times 10^8$ virus units per egg corresponding to 300 µg of purified virus.

Figure 6:
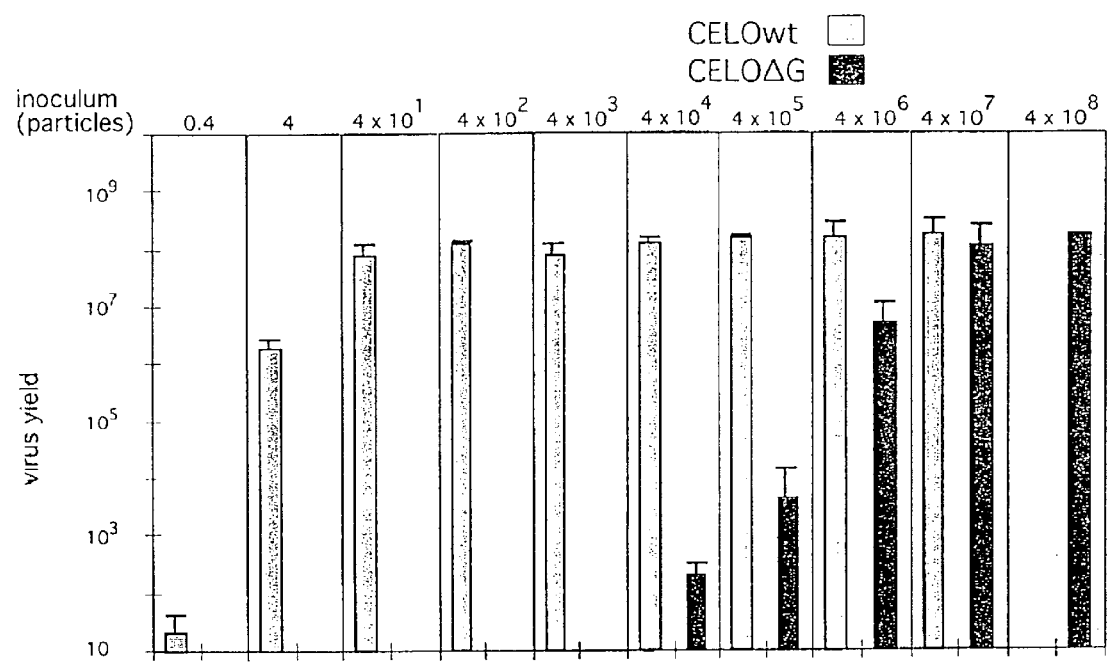
FIG. 6. Analysis of CELO AIM65 growth in chicken embryos.

Embryos were inoculated with either CELO AIM46 or with CELO AIM65. Five days later, allantoic fluid was harvested and assayed for infectious virus. CELO AIM46 produces a maximum yield of virus with inocula of $4 \times 10^1$ particles and higher (FIG. 6). In contrast, comparable levels of CELO AIM65 replication was only observed with inocula of $4 \times 10^7$ particles and above (FIG. 6). Thus it could be shown that Gam1 is required for CELO replication both in LMH cells and in chicken embryos.

EXAMPLE 7

Complementation of CELO AIM65 growth by heat shock.

The previous experiments demonstrate that Gam1 expression affects the levels and localization of hsp40 and hsp70 and that Gam1 expression is essential for CELO replication. These observations raise the possibility that increasing the levels of hsp70 and hsp40 might be a necessary function of Gam1 during CELO replication. To address this question directly, it was determined if a heat shock sufficient to elevate hsp70 and hsp40 could replace Gam1 in CELO replication.

Figure 7:
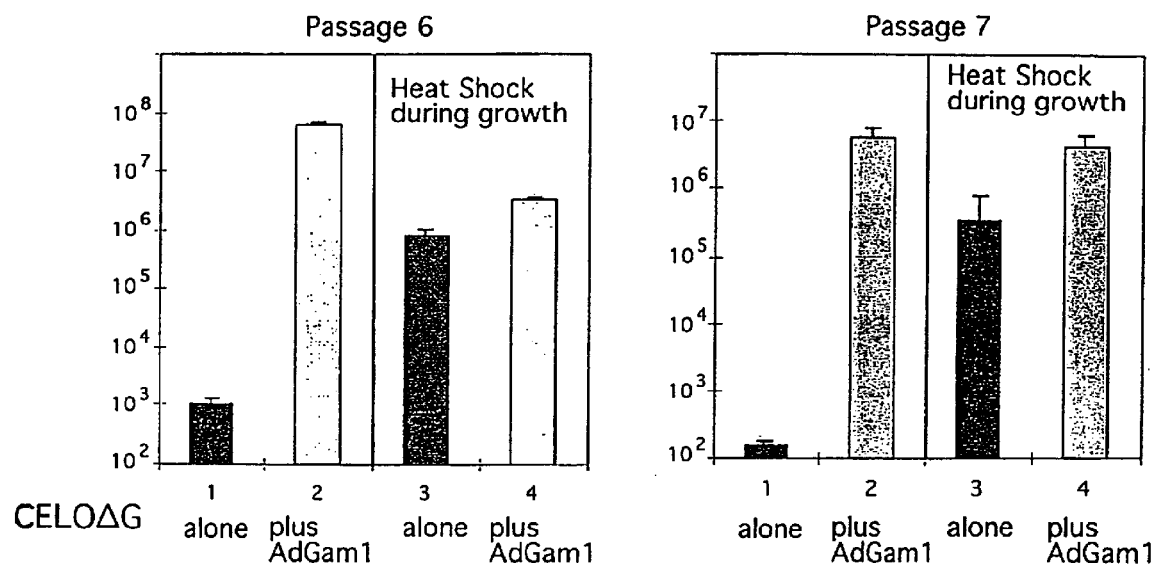
FIG. 7. Complementation of CELO AIM65 growth by heat shock.

The genomes of CELO AIM46 or CELO AIM65 were transfected into LMH cells with AdGam1 added to one of the CELO AIM65 cultures to complement the Gam1 defect as in Example 5. On the second day, one sample of each type of culture was exposed to 45° C. for 90 minutes. After four days at 37° C., lysates were prepared, tested for luciferase activity, and then aliquots of the lysates were added to fresh monolayers of LMH cells with the same series of test complementations (+/− heat shock, +/− AdGam1). This procedure was repeated for multiple passages; FIG. 7 shows luciferase data obtained from Passage 6 and Passage 7.

Similar to the results shown in FIG. 5, CELO AIM65 does not replicate, and the missing Gam1 function can be provided in trans by AdGam1. A short exposure of the infected cells to 45° C. effectively complements the Gam1 defect similarly to AdGam1 complementation (FIG. 7, compare lanes 2 and 3). Thus, the essential Gam1 functions during CELO infection can be replaced by a heat shock.

EXAMPLE 8

Complementation of CELO AIM65 growth in by heat shock in a single round of infection.

Heat shock complementation was used to amplify a CELO AIM65 culture for purification of the virus on CsCl gradients. Purified CELO AIM65 virus was then compared to CELO AIM46 in a single cycle of virus replication.

LMH cells were infected with either CELO AIM46 and CELO AIM65. The cells were either incubated at 37° C. for 4 days (d lanes 1–3; e lanes 1, 2) or exposed to a 90 minute, 45° C. heat shock either 24 hours before infection (d lanes 4–6; e lanes 3, 4); 24 hours after the infection (d lanes 7–9, e lanes 5, 6); or 2 hours before infection (d lanes 10–12; e lanes 7, 8). After 4 days at 37° C., lysates of the cells were prepared and equal aliquots analyzed by immunoblotting for the presence of CELO capsid proteins (upper panel) or tested for the ability to transduce the luciferase gene into fresh LMH cells (lower panel).

Figure 8:
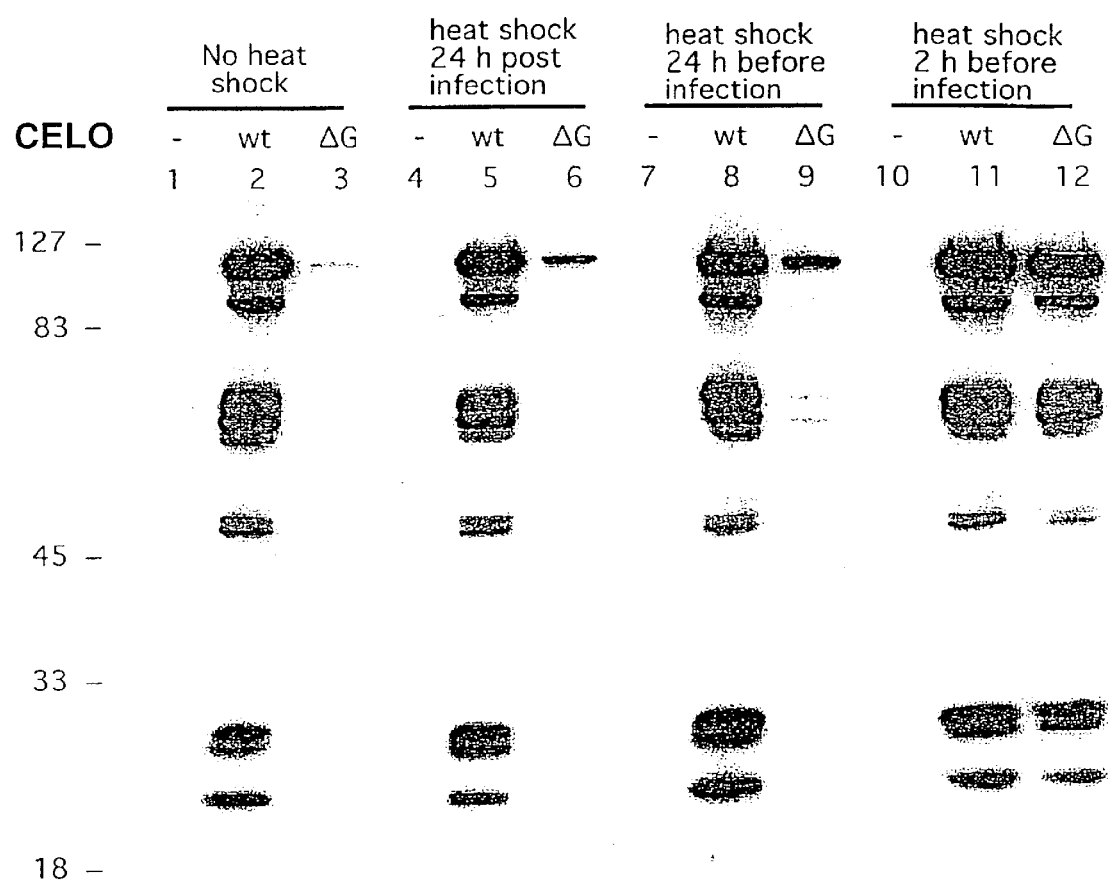
FIG. 8. Complementation of CELO AIM65 growth by heat shock in a single round of infection.
Figure 8:
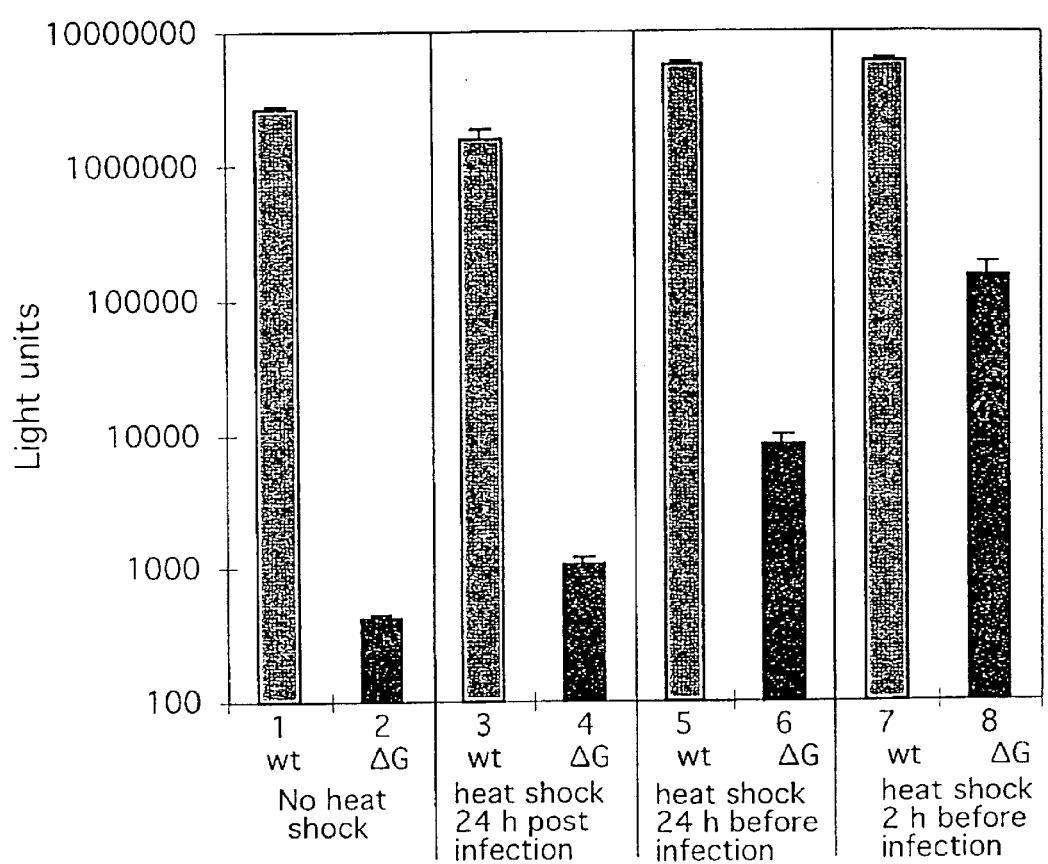

The production of CELO AIM65, which was almost undetectable in non-heated cultures (FIG. 8a, lane 3; 8b, lane 2), was stimulated by the heat shock (FIG. 8a, lanes 6, 9 and 12 and 8b, lanes 4, 6 and 8), with the greatest stimulation observed when the heat shock was applied 2 hours before virus infection (FIG. 8a, lane 12; FIG. 8b, lane 8). Thus it becomes clear that in a single round of virus replication, the essential function of Gam1 in viruys replication can be replaced by a heat shock.

EXAMPLE 9

Complementation of CELO AIM65 growth by hsp40 expression but not by hsp70.

LMH cells were infected with 1 virus particle/cell of CELOAIM65 either alone or plus 10,000 particles/cell of AdEGFP, AdGam1, Adhsp40, or Adhsp70. For each passage, lysates were prepared 5 days post-infection, luciferase was measured (average of three measurements with a standard deviation indicated) and a fresh monolayer of LMH cells was infected (plus the indicated second virus). It is clear from the data that AdGam1 complements the missing Gam1 functions in CELO AIM65. Passageable luciferase activity was obtained, indicating the formation of new infectious virus particles. Slightly less initial activity was observed with Adhsp40 complementation, however, by passage number 5, the Adhsp40 complementation produced passageable luciferase activity comparable to the AdGam1 complementation. Complementation with Adhsp70 did not produce passageable virus demonstrating that hsp70 alone is not sufficient to replace Gam1 functions. Complementation with the control virus AdEGFP also failed, indicating that functions or gene expression from the adenovirus vector cannot replace Gam1.

It is concluded from these results that one of the heat shock proteins known to be induced by Gam1 expression, hsp40, can partially replace the functions of Gam1 in CELO replication.

EXAMPLE 10

Complementation of CELO growth by direct replacement of Gam1 with a hsp40 cDNA.

An alternate method of assessing the complementation is to include the test gene within the genome of CELOAIM65. This approach eliminates the possibility that background gene expression from the adenovirus vector used in the previous example could be influencing the complementation process. Thus, the CELOAIM65 genome was modified, replacing the luciferase cassette (which had been inserted during the disruption of the Gam1 coding region) with either and hsp40 or an hsp70 expression cassette to produce pCELOdGhsp40 and pCELOdGhsp70. Establishment of virus growth was performed by linearizing the genomes with SpeI and transfecting them into LMH cells. pCELOdGhsp40 readily generated replicating virus as evidenced by cytopathic effect and subsequent growth and purification of CELOdGhsp40. However, three independent attempts to establish a CELOdGhsp70 virus culture failed, indicating that direct complementation of Gam1 functions by hsp70 was not possible. This is consistent with the complementation results shown in Example 9 with hsp40 but not hsp70 showing the capacity to complement Gam1.

The growth of CELOdGhsp40 was compared directly with the growth of CELOwt, and CELOAIM65. LMH cells were infected with 5 particles/cell of CELOwt, CELOdG or CELOdGhsp40. After 5 days at 37° C., equal quantities of lysate protein were analyzed by immunoblotting for virus capsid proteins. It is observed that both CELOwt and CELOdGhsp40 generate a signal for the viral capsid proteins, indicating that both viruses have proceeded in the replication cycle to activate late gene expression. The signal derived from CELOdGhsp40 is approximately 1/20 of signal observed with CELOwt, indicating that the complementation is not complete. CELOAIM65 produced no detectable viral late genes products.

It can be concluded that hsp40 when directly expressed from the CELO genome is capable of partially replacing the functions of Gam1. This is consistent with the data presented in Example 9.

REFERENCES

1. Baker, A., M. Saltik, H. Lehrmann, I. Killisch, V. Mautner, G. Lamm, G. Christofori, and M. Cotten. 1997. Gene Therapy 4: 773–782.
2. Bett A. J., W. Haddara, L. Prevec, F. L. Graham. 1994. Proc Natl Acad Sci USA 91:8802–8806
3. Boussif O., F. Lezoualc'h, M. A. Zanta, M. D. Mergny, D. Scherman, B. Demeneix, and J.-P.Behr. 1995. Proc. Natl. Acad. Sci. U S A. 92: 7297–7301.
4. Caravokyri, C. and K. N. Leppard. 1995. J. Virol. 69: 6627–6633.
5. Chartier C., E. Degryse, M. Gantzer, A. Dieterle, A. Pavirani, and M. Mehtali. 1996. J. Virol. 70: 4805–4810.
6. Chiocca, S., R. Kurzbauer, G. Schaffner, A. Baker, V. Mautner, and M. Cotten. 1996. J. Virol. 70: 2939–2949.
7. Chiocca, S., A. Baker, and M. Cotten. 1997. J. Virol. 71: 3168–3177.
8. Colby, W. W. and T.Shenk. 1981. J. Virol. 39: 977–980.
9. Cotten, M., E. Wagner, K. Zatloukal, and M. L. Birnstiel. 1993. J. Virol. 67:3777–3785.
10. Cowen, B., B. W. Calnek, N. A. Menendez and R. F. Ball. 1978. Avian Diseases 22: 459–470.
11. Crouzet J., L. Naudin, C. Orsini, E. Vigne, L. Ferrero, A. Le Roux, P. Benoit, M. Latta, C, Torrent, D. Branellec, P. Denefle, J. F. Mayaux, M. Perricaudet, and P. Yeh, 1997. Proc Natl Acad Sci USA 94: 1414–1419.
12. DeGregori J., G. Leone, A. Miron, L. Jakoi, and J. R. Nevins. 1997. Proc Natl Acad Sci USA 94: 7245–7250.
13. Degryse, E. 1996. Gene 170: 45–50.
14. de Wet J. R., K. V. Wood, M. DeLuca, D. R. Helinski, and S. Subramani. 1987. Mol Cell Biol 7:725–737.
15. Fisher K. J., H. Choi, J. Burda, S. J. Chen, and J. M. Wilson 1996. Virology 217: 11–22.
16. Ghosh-Choudhury, G., Y. Haj-Ahmad, and F. L. Graham. 1987. EMBO J. 6: 1733–1739.
17. Gillen, J. R., D. K. Willis, and A. J. Clark. 1974. in Mechanisms in Genetic Recombination (R. F. Greil, ed.) Plenum, New York, pp123–135.
18. Gluzman, Y., H. Reichl, and D. Solnick, 1982. Helper-free adenovirus type 5 vectors. p187–192. in Y. Gluzman (ed.) Eukaryotic Viral Vectors. Cold Spring Harbor Laboratory Press, Cold Spring Harbor, N.Y.
19. Graham F. L., J. Smiley, W. C. Russell, and R. Nairn. 1977. J. Gen. Virol. 36:59–74.
20. Grubb B. R., R. J. Pickles, H. Ye, J. R. Yankaskas, R. N. Vick, J. F. Engelhardt, J. M. Wilson, L. G. Johnson, and R. C. Nature 371: 802–806.

21. Hardy S., M. Kitamura, T. Harris-Stansil, Y. Dai, M. L. Phipps. 1997. J Virol 71: 1842–1849.
22. Hay, R. T., N. D. Stow, and I. M. McDougall. 1984. J. Mol. Biol. 175: 493–510.
23. He T. C., S. Zhou, L. T. da Costa, J. Yu, K. W. Kinzler, and B. A. Vogelstein. 1998. Proc Natl Acad Sci USA 95:2509–2514.
24. Hess, M., A. Cuzange, R. W. H. Ruigrok, J. Chroboczek and B. Jacrot. 1995. J. Mol. Biol. 252:379–385.
25. Horwitz, M. S. 1996. Adenoviruses. pp2149–2171 in Fields Virology, Third Edition. edited by B. N. Fields, D. M. Knipe, P. M. Howley et al., Lippincott-Raven Publishers, Philadelphia.
26. Hunt, C. & Morimoto, R. I. Conserved features of eukaryotic hsp70 genes revealed by comparison with the nucleotide sequence of human hsp70. *Proc. Natl. Acad. Sci. U.S.A.* 82, 6455–6459 (1985)
27. Imler J. L., C. Chartier, A. Dieterle, D. Dreyer, M. Mehtali, and A. Pavirani. 1995. Gene Ther. 2: 263–268.
28. Kawaguchi T., K. Nomura, Y. Hirayama, T. Kitagawa. 1987. Cancer Res. 47: 4460–4464.
29. Karlsson S., R. K. Humphries, Y. Gluzman, and A. W. Nienhuis. 1985. Proc Natl Acad Sci USA 82: 158–162.
30. Khatri A., Z. Z. Xu, and G. W. Both. 1997. Virology 239: 226–237.
31. Klonjkowski B., P. Gilardi-Hebenstreit, J. Hadchouel, V. Randrianarison, S. Boutin, P. Yeh, M. Perricaudet, and E. J. Kremer. 1997. Hum. Gene Ther. 8: 2103–2115
32. Kovesdi I., D. E. Brough, J. T. Bruder, and T. J. Wickham. 1997. Curr. Opin. Biotechnol. 8: 583–589
33. Kumar-Singh R., and J. S. Chamberlain. 1996. Hum Mol Genet 5: 913–921.
34. Laver, W. G., H. B. Younghusband and N. G. Wrigley. 1971. Virology 45: 598–614.
35. Lemay P., M. L. Boudin, M. Milleville, and P. Boulanger. 1980. Virology 101: 131–143.
36. Li, P., A. J. D. Bellett and C. R. Parish. 1984a. J. Gen. Virol. 65: 1803–1815.
37. Li, P., A. J. D. Bellett and C. R. Parish. 1984b. J. Virol. 52: 638–649.
38. Li, P., A. J. D. Bellett and C. R. Parish. 1984c. J. Virol. 65: 1817–1825.
39. Lieber A., C. Y. He, I. Kirillova, and M. A. Kay. 1996. J Virol 70: 8944–8960.
40. McFerran, J. B. and B. M. Adair. 1977. Avian Pathology 6: 189–217.
41. Michou, A.-I., Lehrmann, H., Saltik, M. & Cotten, M. Mutational analysis of the avian adenovirus CELO, which provides a basis for gene delivery vectors. *J. Virol.* 73, 1399–1410 (1999).
42. Mittal S. K., L. Prevec, F. L. Graham, and L. A. Babiuk. 1995. J. Gen. Virol. 76:93–102.
43. Miyake S., M. Makimura, Y. Kanegae, S. Harada, Y. Sato, K. Takamori, C. Tokuda, and I. Saito. 1996. Proc Natl Acad Sci USA 93: 1320–1324.
44. Oliner, J. D., K. W. Kinzler, and B. Vogelstein. 1993. Nucleic Acids Research 21: 5192–5197.
45. Ohtsuka K. Cloning of a cDNA for heat-shock protein hsp40, a human homologue of bacterial DnaJ. *Biochem. Biophys. Res. Commun.* 197, 235–40 (1993).
46. Parks R. J., L. Chen, M. Anton, U. Sankar, M. A. Rudnicki, F. L. Graham. 1996. Proc Natl Acad Sci USA 93: 13565–13570.
47. Petersson, U. and R. J. Roberts. 1986. Adenovirus gene expression and replication: a historical review. in DNA Tumor Viruses: Control of Gene Expression and Replication pp 37–57. Cold Spring Harbor Laboratory Press, Cold Spring Harbor, N.Y.
48. Plank C., K. Zatloukal, M. Cotten, K. Mechtler, and E. Wagner. 1992. Bioconjugate Chemistry. 3: 533–539.
49. Polyak K., Y. Xia, J. L. Zweier, K. W. Kinzler, and B. Vogelstein. 1997. Nature 389: 300–305.
50. Robinson A. J., H. B. Younghusband, and A. J. Bellett. 1973. Virology 56:54–69.
51. Schaack J., S. Langer, X. Guo. 1995. J Virol. 69: 3920–3923.
52. Shenk, T. 1995. Group C adenovirus as vectors for gene therapy.pp 2111–2148 in Viral Vectors (eds. M. G. Kaplitt and A. D. Loewy) pp. 43–54. Academic Press, San Diego.
53. Shenk, T. 1996. Adenoviridae: The viruses and their is replication. in Fields Virology, Third Edition. edited by B. N. Fields, D. M. Knipe, P. M. Howley et al., Lippincott-Raven Publishers, Philidelphia.
54. Soberon X., L. Covarrubias, F. Bolivar. 1980. Gene 9: 287–305.
55. Van Doren K., D. Hanahan, and Y. Gluzman. 1984. J Virol. 50: 606–614.
56. Vrati S., E. S. Macavoy, Z. Z. Xu, C. Smole, D. B. Boyle, and G. W. Both. 1996b, Virology 220: 200–203.
57. Weiss R. S., S. S. Lee, B. V. Prasad, and R. T. Javier. 1997. J. Virol. 71:1857–1870.
58. Wilson C., and M. A. Kay. 1995. Nature Medicine. 1: 887–889.
59. Xu Z. Z., A. Hyatt, D. B. Boyle and G. W. Both. 1997. Virology 230: 62–71.
60. Yates, V. J. and D. E. Fry. 1957. Am. J. Vet. Res. 18: 657–660.
61. Zabner J., B. G. Zeiher, E. Friedman, and Welsh M. J. 1996. J.Virol. 70: 6994–7003.
62. Zabner J., P. Freimuth, A. Puga, A. Fabrega, and Welsh M J. 1997. J. Clin. Invest. 100: 1144–1149.
63. Zheng B., S. K. Mittal, F. L. Graham, and L. Prevec. 1994. Virus Res 31: 163–186
64. Lillehoj H. S., and Trout J. M., 1996, Clin. Microbiol. Rev., July 9(3): 349–360
65. Taylor M. A., and Catchpole J. 1994, Appl. parasitol, June 35(2): 73–86
66. Shirley M. W., 1992, Br. Vet. J., November 148(6): 479–499
67. Lasher H. N. and Davis V. S., 1997, Avian Dis., January 41(1): 11–19
68. Buge S. L., Richardson E., Alipanah S., Markham P., Cheng S., Kalyan N., Miller C. J., Lubeck M., Udem S., Eldridge J., Robert-Guroff M., 1997, J Virol November; 71(11):8531–41
69. Celli G., LaRochelle W. J., Mackem S., Sharp R., Merlino G., 1998, EMBO J. March 16;17(6):1642–55
70. de Quinto S. L., Martinez-Salas E., 1998, Gene September 14;217(1–2):51–6
71. Gerber H. P., Hillan K. J., Ryan A. M., Kowalski J., Keller G. A., Rangell L., Wright B. D., Radtke F., Aguet M., Ferrara N., 1999, Development March;126(6): 1149–59
72. Gerdts V., Jons A., Makoschey B., Visser N., Mettenleiter T. C., 1997, J Gen Virol September;78 (Pt 9):2139–46
73. Havenga M. J. E., Vogels R., Braakman E., Kroos N., Valerio D., Hagenbeek A., van Es H. H. G., 1998, Gene November 19;222(2):319–27
74. Levenson V. V., Transue E. D., Roninson I. B., 1998, Hum Gene Ther May 20;9(8):1233–6
75. Li X., Wang W., Lufkin T., 1997, Biotechniques November;23(5):874–8, 880, 882
76. Lubeck M. D., Natuk R., Myagkikh M., Kalyan N., Aldrich K., Sinangil F., Alipanah S., Murthy S. C., Chanda P. K., Nigida S. M. Jr., Markham P. D., Zolla- Pazner S., Steimer K., Wade M., Reitz M. S. Jr., Arthur L. O., Mizutani S., Davis A., Hung P. P., Gallo R. C., Eichberg J., Robert-Guroff M., 1997, Nat Med June;3(6): 651–8

77. Ohtsuka K. Cloning of a cDNA for heat-shock protein hsp40, a human homologue of bacterial DNA J. *Biochem. Biophys. Res. Commun.* 197, 235–40 (1993)

78. Plank C., Zatloukal K., Cotten M., Mechtler K., and Wagner E., 1992, Bioconjugate Chemistry. 3: 533–539.

79. Robbins A. K., Watson R. J., Whealy M. E., Hays W. W., Enquist L. W., 1986, J Virol May;58(2):339–47

80. Schreurs C., Mettenleiter T. C., Zuckermann F., Sugg N., Ben-Porat T., 1988, J Virol July;62(7):2251–7

81. Vermeulen A. N., 1998, Int J Parasitol July;28(7): 1121–30

82. Talsma H., et al., 1997, Int. J. of Pharmaceutics 157, 233–238

83. Michou, A.-I., Lehrmann, H., Saltik, M. and Cotten, M. 1999. Mutational analysis of the avian adenovirus CELO, which provides a basis for gene delivery vectors. *J. Virol.* 73, 1399–1410.

84. Stratford-Perricaudet, L. D., Makeh, I., Perricaudet, M. and Briand, P. 1992. Widespread long-term gene transfer to mouse skeletal muscles and heart. *J. Clin. Invest.* 90, 626–30.

85. Evan, G. I., Lewis, G. K., Ramsay, G. & Bishop, J. M. 1985. Isolation of monoclonal antibodies specific for human c-myc proto-oncogene product. Mol. Cell. Biol. 5, 3610–3616.

What is claimed is:

1. A recombinant CELO virus or CELO virus DNA, characterized in that the virus or DNA comprises a CELO wild type genome, wherein the genome contains at least one deletion, said deletion consisting of nucleotides 37,391–37,972 of the CELO wild type virus genome, wherein said deletion results in a complete loss of Gam1 expression or prevents the expression of a functional Gam1 protein, wherein the genome can be complimented by heat shock or heat shock protein 40.

2. The recombinant CELO virus or CELO virus DNA of claim 1, wherein the region spanning nucleotides 37,391–38,239 of the CELO wild type virus genome is deleted.

3. The recombinant CELO virus or CELO virus DNA of claim 1, characterized in that it contains a modification in the Gam1 transcriptional control sequences.

4. The recombinant CELO virus or CELO virus DNA of claim 1, characterized in that it further contains a deletion of or within a region selected from the regions spanning nucleotides 41731–43684, nucleotides 41523–43684, nucleotides 41002–43684 and nucleotides 40065–43684.

5. The recombinant CELO virus or CELO virus DNA of claim 1, characterized in that it further contains a deletion spanning nucleotides 794–1330.

6. The recombinant CELO virus DNA of claim 1 contained on a plasmid that can be replicated in procaryotic or eucaryotic cells.

7. The recombinant CELO virus or CELO virus DNA of claim 1, characterized in that it contains a foreign DNA insertion within said region.

8. The recombinant CELO virus or CELO virus DNA of claim 7 chararcterized in that the foreign DNA encodes an antigen derived from an animal pathogen.

9. The recombinant CELO virus or CELO virus DNA of claim 8 characterized in that the pathogen is avian.

10. The recombinant CELO virus or CELO virus DNA of claim 7 characterized in that the foreign DNA encodes a human protein.

11. The recombinant CELO virus or CELO virus DNA of claim 10, characterized in that the foreign DNA encodes a therapeutically active protein.

12. The recombinant CELO virus or CELO virus DNA of claim 11, characterized in the foreign DNA encodes an immunostimulatory protein.

13. The recombinant CELO virus or CELO virus DNA of claim 12, characterized in that the immunostimulatory protein is a cytokine.

14. The recombinant CELO virus or CELO virus DNA of claim 10, characterized in that the foreign DNA encodes a tumor antigen or an immunogenic fragment thereof.

15. The recombinant CELO virus or CELO virus DNA of claim 10, characterized in that the foreign DNA encodes an antigen derived from a human pathogen.

16. A recombinant CELO virus or CELO virus DNA, characterized in that the virus or DNA comprises a CELO wild type genome, wherein the genome contains at least one deletion, said deletion consisting of nucleotides 36,818–37,972 of the CELO wild type virus genome, wherein said deletion results in a complete loss of Gam1 expression or prevents the expression of a functional Gam1 protein, wherein the genome can be complimented by heat shock or heat shock protein 40.

17. The recombinant CELO virus or CELO virus DNA of claim 16, characterized in that it contains a modification in the Gam1 transcriptional control sequences.

18. The recombinant CELO virus or CELO virus DNA of claim 16, characterized in that it further contains a deletion of or within a region selected from the regions spanning nucleotides 41731–43684, nucleotides 41523–43684, nucleotides 41002–43684 and nucleotides 40065–43684.

19. The recombinant CELO virus or CELO virus DNA of claim 16, characterized in that it further contains a deletion spanning nucleotides 794–1330.

20. The recombinant CELO virus DNA of claim 16 contained on a plasmid that can be replicated in procaryotic or eucaryotic cells.

21. The recombinant CELO virus DNA of claim 20, wherein said plasmid is pAIM65 or a derivative thereof, wherein said derivative contains a deletion of nucleotides 36,818–37,972 of the wild type CELO virus genome.

22. The recombinant CELO virus or CELO virus DNA of claim 16, characterized in that it contains a foreign DNA insertion within said region.

23. The recombinant CELO virus or CELO virus DNA of claim 22, characterized in that the foreign DNA encodes an antigen derived from an animal pathogen.

24. The recombinant CELO virus or CELO virus DNA of claim 23 characterized in that the pathogen is avian.

25. The recombinant CELO virus or CELO virus DNA of claim 22 characterized in that the foreign DNA encodes a human protein.

26. The recombinant CELO virus or CELO virus DNA of claim 25, characterized in that the foreign DNA encodes a therapeutically active protein.

27. The recombinant CELO virus or CELO virus DNA of claim 26, characterized in the foreign DNA encodes an immunostimulatory protein.

28. The recombinant CELO virus or CELO virus DNA of claim 27, characterized in that the immunostimulatory protein is a cytokine.

29. The recombinant CELO virus or CELO virus DNA of claim 25, characterized in that the foreign DNA encodes a tumor antigen or an immunogenic fragment thereof.

30. The recombinant CELO virus or CELO virus DNA of claim 25, characterized in that the foreign DNA encodes an antigen derived from a human pathogen.

* * * * *